(12) United States Patent
Solem et al.

(10) Patent No.: US 10,569,005 B2
(45) Date of Patent: Feb. 25, 2020

(54) DEVICE AND METHOD FOR DISRUPTION DETECTION

(71) Applicant: GAMBRO LUNDIA AB, Lund (SE)

(72) Inventors: Kristian Solem, Trelleborg (SE); Bo Olde, Lund (SE)

(73) Assignee: Gambro Lundia AB, Lund (SE)

( * ) Notice: Subject to any disclaimer, the term of this patent is extended or adjusted under 35 U.S.C. 154(b) by 300 days.

(21) Appl. No.: 15/569,222

(22) PCT Filed: Jun. 3, 2016

(86) PCT No.: PCT/EP2016/062622
§ 371 (c)(1),
(2) Date: Oct. 25, 2017

(87) PCT Pub. No.: WO2016/206950
PCT Pub. Date: Dec. 29, 2016

(65) Prior Publication Data
US 2018/0296744 A1 Oct. 18, 2018

(30) Foreign Application Priority Data

Jun. 25, 2015 (SE) ...................................... 1550884

(51) Int. Cl.
*A61M 1/36* (2006.01)
*A61B 5/0215* (2006.01)
*G16H 40/63* (2018.01)

(52) U.S. Cl.
CPC ........ *A61M 1/3639* (2013.01); *A61M 1/3656* (2014.02); *A61B 5/0215* (2013.01);
(Continued)

(58) Field of Classification Search
CPC .............. A61M 1/3639; A61M 1/3656; A61M 2205/18; A61M 2205/3331;
(Continued)

(56) References Cited

U.S. PATENT DOCUMENTS

| 10,314,965 | B2* | 6/2019 | Holmer | ................ | A61B 5/7217 |
| 2004/0230128 | A1* | 11/2004 | Brockway | ................ | A61N 1/05 |
| | | | | | 600/510 |

(Continued)

FOREIGN PATENT DOCUMENTS

| WO | 2011080191 | 7/2011 |
| WO | 2012163738 | 12/2012 |

(Continued)

OTHER PUBLICATIONS

C. James, et al., "Independent component analysis for biomedical signals," Physiological Measurement, Institute of Physics Publishing, Bristol, GB, vol. 26, No. 1, Feb 1, 2005, pp. R15-39, XP020092142.
(Continued)

*Primary Examiner* — Philip R Wiest
(74) *Attorney, Agent, or Firm* — K&L Gates LLP

(57) ABSTRACT

A monitoring device detects a disruption of a fluid connection between first and second fluid containing systems using one or more pressure sensors arranged in the first fluid containing system to detect first pulses from the first fluid containing system and second pulses from the second fluid containing system. The monitoring device receives (501) pressure signal(s) from the pressure sensor(s), populates (504) signal vectors by signal segments in the pressure signal(s) and computes (505) one or more eigenvectors and/or one or more eigenvalues for the signal vectors by a source separation algorithm. The monitoring device detects (506) the disruption based on a monitoring parameter, which is computed as a function of the eigenvector(s) and/or eigenvalue(s) to be responsive to the second pulses in the pressure signal(s). The monitoring device may be associated with or included in an apparatus for extracorporeal blood processing, such as a dialysis machine.

25 Claims, 10 Drawing Sheets

(52) U.S. Cl.
CPC ...... *A61B 5/02152* (2013.01); *A61M 2205/18* (2013.01); *A61M 2205/3331* (2013.01); *A61M 2205/50* (2013.01); *A61M 2230/30* (2013.01); *G16H 40/63* (2018.01)

(58) Field of Classification Search
CPC .......... A61M 2205/50; A61M 2230/30; A61B 5/0215; A61B 5/02152; G16H 40/63
See application file for complete search history.

(56) References Cited

U.S. PATENT DOCUMENTS

| | | | | |
|---|---|---|---|---|
| 2005/0288600 | A1* | 12/2005 | Zhang | A61B 5/0006 600/510 |
| 2010/0022934 | A1 | 1/2010 | Hogard | |
| 2011/0315611 | A1 | 12/2011 | Fulkerson et al. | |
| 2012/0302846 | A1* | 11/2012 | Volnner | A61B 5/02416 600/324 |
| 2014/0296726 | A1* | 10/2014 | Brockway | A61B 7/00 600/514 |
| 2016/0218431 | A1* | 7/2016 | Gaddi | H01Q 1/243 |

FOREIGN PATENT DOCUMENTS

| | | |
|---|---|---|
| WO | 2014009111 | 1/2014 |
| WO | 2014095524 | 6/2014 |
| WO | 2015032948 | 3/2015 |

OTHER PUBLICATIONS

H. Abdi et al., "Principal Component Analysis," Wiley Interdisciplinary Reviews: Computational Statistics, vol. 2, No. 4, Jun. 30, 2010, pp. 433-459, XP055292434.

G.D. Clifford, "Chapter 15—Blind Source Separation: Principal & Independent Component Analysis," Biomedical Signal and Image Processing, Spring 2008, pp. 1-47.

International Search Report issued in International Patent Application No. PCT/EP2016/062622 dated Aug. 12, 2016. 4 pages.

Written Opinion issued in International Patent Application No. PCT/EP2016/062622 dated Aug. 12, 2016. 8 pages.

* cited by examiner

DEVICE AND METHOD FOR DISRUPTION DETECTION

PRIORITY CLAIM

The present application is a National Phase of International Application No. PCT/EP2016/062622, filed Jun. 3, 2016, which claims priority to Swedish Patent Application No. 1550884-9, filed Jun. 25, 2015, the entire contents of each of which are incorporated herein by reference and relied upon.

TECHNICAL FIELD

The present invention relates to techniques for detecting a disruption of a fluid connection between a first fluid containing system comprising a first pulse generator and a second fluid containing system comprising a second pulse generator, by processing at least one pressure signal from a set of pressure sensors arranged in the first fluid containing system. The first fluid containing system may e.g. be an extracorporeal circuit for blood processing.

BACKGROUND ART

In extracorporeal blood processing, blood is taken out of a human subject, processed (e.g. treated) and then reintroduced into the subject by means of an extracorporeal blood flow circuit ("EC circuit") which is part of a machine for blood processing. Generally, the blood is circulated through the EC circuit by a blood pump. In certain types of extracorporeal blood processing, the EC circuit includes an access device for blood withdrawal (e.g. an arterial needle or catheter) and an access device for blood reintroduction (e.g. a venous needle or catheter), which are inserted into a dedicated blood vessel access (e.g. fistula or graft) on the subject. The access devices form a fluid connection between the EC circuit and the cardiovascular system of the subject. This type of EC circuit is, e.g., used in extracorporeal blood treatments such as hemodialysis, hemodiafiltration, hemofiltration, plasmapheresis, bloodbanking, blood fraction separation (e.g. cells) of donor blood, apheresis, extracorporeal blood oxygenation, assisted blood circulation, extracorporeal liver support/dialysis, ultrafiltration, etc.

It is vital to minimize the risk for malfunctions in the fluid connection that may lead to a potentially life-threatening condition of the subject. A particularly serious condition may arise if the EC circuit is disrupted downstream of the blood pump while the blood pump is running, e.g. by the access device for blood reintroduction coming loose from the blood vessel access. Such a venous-side disruption, which is commonly referred to as a Venous Needle Dislodgement (VND), may cause the subject to be drained of blood within minutes. A disruption on the arterial side, e.g. by the access device for blood withdrawal coming loose from the blood vessel access, may also present a patient risk, by air being sucked into the EC circuit and transported into the cardiovascular system.

Machines for extracorporeal blood treatment typically include a safety system that monitors the status of the fluid connection between the EC circuit and the subject and triggers an alarm and/or an appropriate safety action whenever a potentially dangerous situation is detected. Such safety systems may operate on pressure signals from pressure sensors in the EC circuit. Conventionally, VND detection is carried out by comparing one or more measured average pressure levels with one or more threshold values. However, it may be difficult to set appropriate threshold values, since the average pressure in the EC circuit may vary between treatments and between subjects, and also during a treatment, e.g. as a result of the patient moving. Further, if an access device comes loose and gets stuck in bed sheets or the patient's clothes, the measured average pressure might not change enough to indicate the potentially dangerous situation.

To overcome these drawbacks, various techniques have been proposed for detecting VND by identifying absence of dedicated pulsations, which originate from the subject, in a pressure signal from a pressure sensor ("venous pressure sensor") on the downstream side of the blood pump in the EC circuit, e.g. in WO97/10013, US2005/0010118, WO2009/156174, WO2010/149726 and US2010/0234786. The dedicated pulsations may e.g. originate from the heart or the breathing system. These known VND detection techniques presume that the heart or breathing pulses can be reliably detected in the pressure signal. To enable reliable detection, it may be necessary to filter the pressure signal to essentially remove all signal interferences. In practice, the accuracy and robustness of the VND detection relies on the efficiency and stability of the filtering technique used for cleaning the pressure signal from signal interferences. The signal interferences typically comprise strong pressure pulsations ("pump pulses") originating from the blood pump, and may also comprise further interfering pressure pulsations, e.g. caused by further pumps, valves, balancing chambers, etc in the EC circuit. It may be a challenging task to remove e.g. the pump pulses, since the rate of the heart pulses and the rate of the blood pump, i.e. the blood flow through the EC circuit, may change over time. If the rate of heart pulses matches the rate of pump pulses, it is not unlikely that the filtering will fail. Complete removal of the pump pulses is also rendered difficult by the fact that the pump pulses generally are much stronger than the heart and breathing pulses in the pressure signal. An advanced filtering technique may thus be required, increasing complexity and potentially introducing stability and convergence issues.

There is a continued need to achieve an improved technique for detecting a disruption of the fluid connection on the arterial side and/or the venous side of the EC circuit, in terms of one or more of the following: ability to handle overlap in frequency and/or time between pump pulses and heart pulses, complexity of the detection technique, response time, processing efficiency and memory usage of the detection technique, accuracy of detection, and robustness of detection.

Corresponding needs may arise in other fields of technology. Thus, generally speaking, there is a need for an improved or alternative technique for detecting a disruption of a fluid connection between a first fluid containing system and a second fluid containing system, based on at least one pressure signal acquired from a set of pressure sensors in the first fluid containing system.

SUMMARY

It is an objective of the invention to at least partly overcome one or more limitations of the prior art.

Another objective is to provide a technique for detecting a disruption of a fluid connection that is capable of meeting one or more of the above-mentioned needs.

One or more of these objectives, as well as further objectives that may appear from the description below, are at least partly achieved by means of monitoring devices, a method of monitoring and a computer-readable medium according to the independent claims, embodiments thereof being defined by the dependent claims.

A first aspect of the invention is a monitoring device for detecting a disruption of a fluid connection between a first fluid containing system comprising a first pulse generator and a second fluid containing system comprising a second pulse generator. The monitoring device comprises: an input for receiving at least one pressure signal from a set of pressure sensors arranged in the first fluid containing system to detect first pulses originating from the first pulse generator and second pulses originating from the second pulse generator; and a signal processor connected to the input. The signal processor is configured to: populate a plurality of signal vectors of identical length such that each of the signal vectors corresponds to a respective signal segment of signal values in the at least one pressure signal; process the signal vectors by a source separation algorithm so as to compute one or more eigenvectors and/or one or more eigenvalues associated with the signal vectors; and detect the disruption based on a monitoring parameter, which is computed as a function of the one or more eigenvectors and/or the one or more eigenvalues to be responsive to the second pulses in the at least one pressure signal.

The first aspect is based on the insight that it is possible to relax the need for more or less perfect removal of signal interferences in a pressure signal before analyzing the pressure signal for disruption detection, by instead applying a proper source separation algorithm to one or more pressure signals and analyzing the resulting data for disruption detection. A source separation algorithm will, to a greater or lesser degree depending on implementation, separate and reproduce source signals that are present and mixed together in the one or more pressure signals. It has surprisingly been found that source separation algorithms that involve computation of eigenvectors and/or eigenvalues have the ability of relaxing the need for filtering of the pressure signal(s) when detecting a disruption of the fluid connection, since at least some of the eigenvectors and/or eigenvalues are indicative of the second pulses (if present). Computation of eigenvectors and/or eigenvalues is a standard procedure per se, and there are many available and established computation methods that are both numerically stable and processing-efficient. The processing of signal vectors by a source separation algorithm does not imply that a full conventional implementation a specific algorithm needs to be applied. The source separation algorithm only needs to be implemented to compute the eigenvectors and/or eigenvalues that are used for computing the monitoring parameter that is responsive to the second pulses in the pressure signal(s).

Principally, any known source separation algorithm that involves computation of eigenvectors and/or eigenvalues may be applied by the monitoring device of the first aspect. Such source separation algorithms include, but are not limited to, Principal Component Analysis (PCA), Independent Component Analysis (ICA), Factor Analysis, Canonical Correlation Analysis (CCA) and Common Spatial Pattern (CSP).

As will be exemplified further below, the monitoring device of the first aspect may operate on a single pressure signal or two or more pressure signals. Thus, as used herein, "a set of pressure sensors" is intended to encompass a single pressure sensor.

In one embodiment, the signal processor is configured, when processing the signal vectors by the source separation algorithm, to compute the one or more eigenvectors and/or the one or more eigenvalues for an estimated covariance matrix comprising estimated covariance values for the signal vectors. The estimated covariance matrix may be given by $f(X^T X)$, wherein X is a matrix with the signal vectors arranged as rows or columns, $X^T$ is a transpose of the matrix X, and $f$ is a linear function. It should be noted that the eigenvectors, and optionally the eigenvalues, may be computed without a need to explicitly populate the estimated covariance matrix. However, the signal processor may be further configured, when processing the signal vectors, to: compute the estimated covariance values, populate the estimated covariance matrix by the estimated covariance values, and process the estimated covariance matrix for computation of the one or more eigenvectors and/or the one or more eigenvalues.

In one embodiment, the source separation algorithm comprises one of Principal Component Analysis, PCA, and Independent Component Analysis, ICA.

In one embodiment, the signal processor is configured to populate the signal vectors such that at least a subset of the signal vectors correspond to mutually time-shifted signal segments in a dedicated pressure signal included among the at least one pressure signal, or in an intermediate signal generated based on the at least one pressure signal. Thus, in this embodiment, at least a subset of the populated signal vectors correspond to mutually time-shifted signal segments within one and the same signal, which is either a pressure signal or an intermediate signal. If the signal filtering device receives at least two pressure signals, the signal processor may be configured to generate the intermediate signal by linearly combining corresponding pressure values in the at least two pressure signals.

In one embodiment, the signal processor is configured to populate the signal vectors such that said at least a subset of the signal vectors correspond to partly overlapping and mutually time-shifted signal segments in the dedicated pressure signal or the intermediate signal.

In one embodiment, the signal processor is configured to populate the signal vectors exclusively based on the mutually time-shifted signal segments in the dedicated pressure signal or the intermediate signal.

Alternatively, when the input receives a plurality of pressure signals from a plurality of pressure sensors, the signal processor may be configured to populate the signal vectors such that each signal vector corresponds to a respective signal segment in a respective one of the pressure signals.

In one embodiment, the signal processor is further configured, when detecting the disruption, to: identify a change to the monitoring parameter over time or by comparing the monitoring parameter to a threshold value.

In one embodiment, the signal processor is configured, when processing the signal vectors, to compute a plurality of eigenvalues, wherein the signal processor is configured to compute the monitoring parameter to represent one of: a magnitude of at least a subset of the plurality of eigenvalues, a difference between pairs of eigenvalues for at least a subset of the plurality of eigenvalues when ordered by magnitude, and a distribution of at least a subset of the plurality of eigenvalues when ordered by magnitude.

In one embodiment, the signal processor is configured, when processing the signal vectors, to compute a plurality of eigenvalues and, optionally, a plurality of eigenvectors, wherein the signal processor is further configured, when computing the monitoring parameter, to order the eigenvectors and/or the eigenvalues by order of magnitude of the eigenvalues. The signal processor may be configured to compute the monitoring parameter based on at least one selected eigenvector among the plurality of eigenvectors and/or at least one selected eigenvalue among the plurality of eigenvalues, and the signal processor may be configured to derive each selected eigenvalue by selecting an eigenvalue having a predefined order number among the plurality of eigenvalues when ordered by magnitude, and/or to derive each selected eigenvector by selecting an eigenvector having a predefined order number among the plurality of eigenvectors when ordered by magnitude of their associated eigenvalues. For example, the signal processor may be configured to compute the monitoring parameter to represent one or more of: a magnitude of the at least one selected eigenvalue, a frequency of the at least one selected eigenvector, and a shape of the at least one selected eigenvector.

In one embodiment, the signal processor is configured to receive, via the input, a reference pressure signal from a reference pressure sensor in the set of pressure sensors in the first fluid containing system, the reference pressure sensor being arranged to detect the second pulses irrespective of the disruption of the fluid connection. The signal processor is configured to: populate a plurality of reference signal vectors of identical length such that each of the reference signal vectors corresponds to a respective signal segment of signal values in the reference pressure signal; and process the reference signal vectors by the source separation algorithm so as to compute at least one of: one or more reference eigenvectors and one or more reference eigenvalues associated with the reference signal vectors. The signal processor is further configured, when detecting the disruption, to compare the one or more eigenvectors to the one or more reference eigenvectors and/or compare the one or more eigenvalues to the one or more reference eigenvalues. In one embodiment, the signal processor is configured to: compute the monitoring parameter as a function of a correlation value resulting from a cross-correlation of the above-mentioned at least one selected eigenvector and the one or more reference eigenvectors.

In one embodiment, the signal processor is further configured, before populating the plurality of signal vectors, to filter the at least one pressure signal so as to decrease a magnitude of the first pulses below a magnitude of the second pulses.

In one embodiment, the signal processor is further configured, before processing the signal vectors, to process the at least one pressure signal and/or the signal vectors to yield an average of zero for signal vector values in the respective signal vector.

In one embodiment, the first fluid containing system is an extracorporeal blood circuit comprising a blood pump configured to pump blood from a blood withdrawal device to a blood return device, wherein the second fluid containing system is a cardiovascular system of a human body, the first pulse generator comprising the blood pump and the second pulses originating from a pulse generator in or attached to the human body, wherein the blood withdrawal device and the blood return device are fluidly connected to the cardiovascular system, and wherein the fluid connection is formed between the blood return device and the cardiovascular system. In a specific implementation, the signal processor is configured to receive, via the input, the at least one pressure signal from a pressure sensor located between the blood pump and the blood return device to sense the pressure of the blood in the extracorporeal blood circuit.

In one embodiment, the signal processor is further configured to generate an output signal indicative of the disruption of the fluid connection.

A second aspect of the invention is a monitoring device for detecting a disruption of a fluid connection between a first fluid containing system comprising a first pulse generator and a second fluid containing system comprising a second pulse generator. The monitoring device comprises: means for receiving at least one pressure signal from a set of pressure sensors arranged in the first fluid containing system to detect first pulses originating from the first pulse generator and second pulses originating from the second pulse generator; means for populating a plurality of signal vectors of identical length such that each of the signal vectors corresponds to a respective signal segment of signal values in the at least one pressure signal; means for processing the signal vectors by a source separation algorithm so as to compute one or more eigenvectors and/or one or more eigenvalues associated with the signal vectors; and means for detecting the disruption based on a monitoring parameter, which is computed as a function of the one or more eigenvectors and/or the one or more eigenvalues to be responsive the second pulses in the at least one pressure signal.

A third aspect of the invention is a method of monitoring a fluid connection between a first fluid containing system comprising a first pulse generator and a second fluid containing system comprising a second pulse generator. The method is performed by a data processor and comprises: receiving at least one pressure signal from a set of pressure sensors arranged in the first fluid containing system to detect first pulses originating from the first pulse generator and second pulses originating from the second pulse generator; populating a plurality of signal vectors of identical length such that each of the signal vectors corresponds to a respective signal segment of signal values in the at least one pressure signal; processing the signal vectors by a source separation algorithm so as to compute one or more eigenvectors and/or one or more eigenvalues associated with the signal vectors; and detecting the disruption based on a monitoring parameter, which is computed as a function of the one or more eigenvectors and/or the one or more eigenvalues to be responsive to the second pulses in the at least one pressure signal.

A fourth aspect of the invention is a computer-readable medium comprising processing instructions for causing a data processor to perform the method of the third aspect.

Any one of the above-identified embodiments of the first aspect may be adapted and implemented as an embodiment of the second to fourth aspects.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

DETAILED DESCRIPTION OF EXAMPLE EMBODIMENTS

Figure 1:
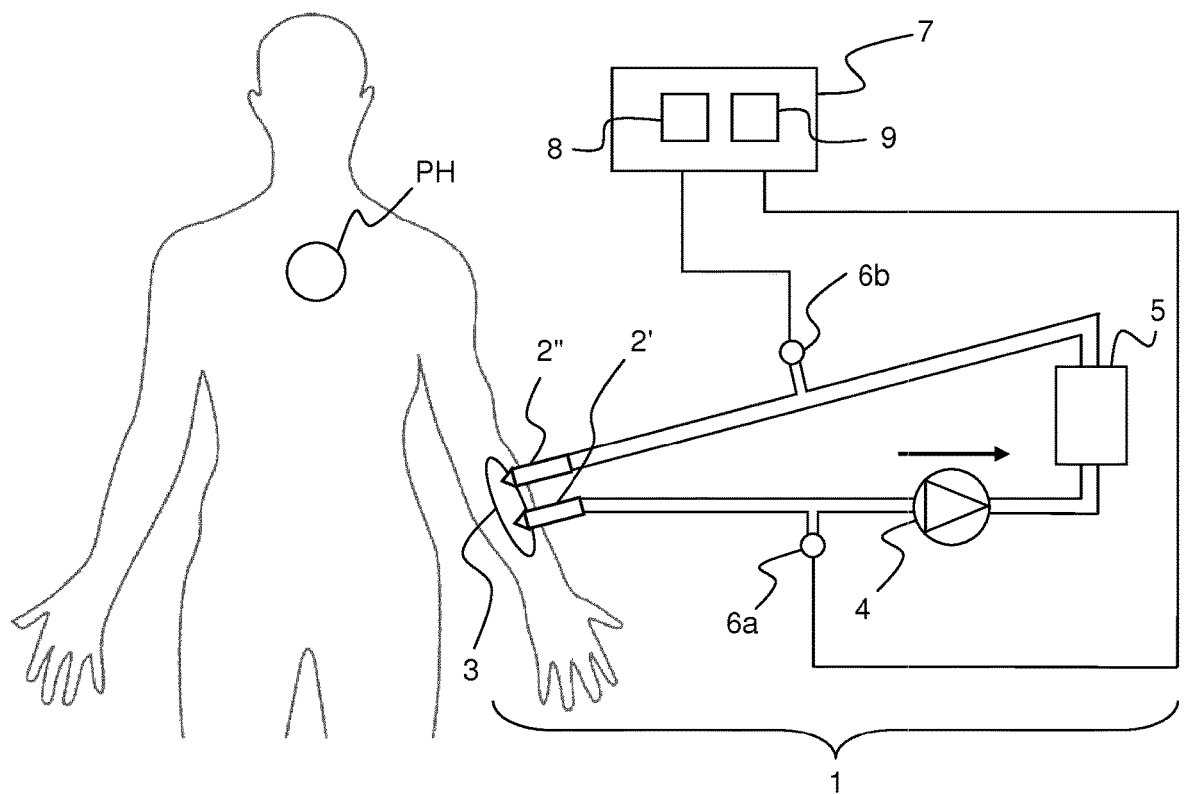
FIG. 1 a schematic diagram of a blood path in an extracorporeal blood processing apparatus attached to a human subject.

Throughout the description, the same reference numerals are used to identify corresponding elements.

FIG. 1 illustrates a human subject which is connected to an extracorporeal fluid circuit 1 by way of access devices 2', 2" inserted into a dedicated vascular access 3 (also known as "blood vessel access") on the subject. The extracorporeal fluid circuit 1 (denoted "EC circuit" in the following) is configured to communicate blood to and from the cardiovascular system of the subject. In one example, the EC circuit 1 is part of an apparatus for blood processing, such as a dialysis machine. In the illustrated example, a blood pump 4 draws blood from the vascular access 3 via access device 2' and pumps the blood via blood lines (tubes) through a blood processing unit 5, e.g. a dialyzer, and back to the vascular access 3 via access device 2". Thus, when both access devices 2', 2" are connected to the vascular access 3, the EC circuit 1 defines a blood path that starts and ends at the vascular access 3. The EC circuit 1 may be seen to comprise a "venous side" which is the part of the blood path located downstream of the blood pump 4, and an "arterial side" which is the part of the blood path located upstream of the pump 4.

Pressure sensors 6a and 6b are arranged to detect pressure waves in the EC circuit 1. As used herein, a "pressure wave" is a mechanical wave in the form of a disturbance that travels or propagates through a material or substance. In the context of the following examples, the pressure waves propagate in the blood in the cardiovascular system of the subject and in the blood path of the EC circuit 1 at a velocity that typically lies in the range of about 3-20 m/s. The pressure sensors 6a, 6b, which are in direct or indirect hydraulic contact with the blood, generate pressure data that forms a pressure pulse for each pressure wave. A "pressure pulse" is thus a set of data samples that define a local increase or decrease (depending on implementation) in signal magnitude within a time-dependent measurement signal ("pressure signal").

The pressure sensors 6a, 6b may be of any type, e.g. operating by resistive, capacitive, inductive, magnetic, acoustic or optical sensing, and using one or more diaphragms, bellows, Bourdon tubes, piezo-electrical components, semiconductor components, strain gauges, resonant wires, accelerometers, etc. For example, the pressure sensors 6a, 6b may be implemented as a conventional pressure sensor, a bioimpedance sensor, or a photoplethysmography (PPG) sensor.

Figure 2:
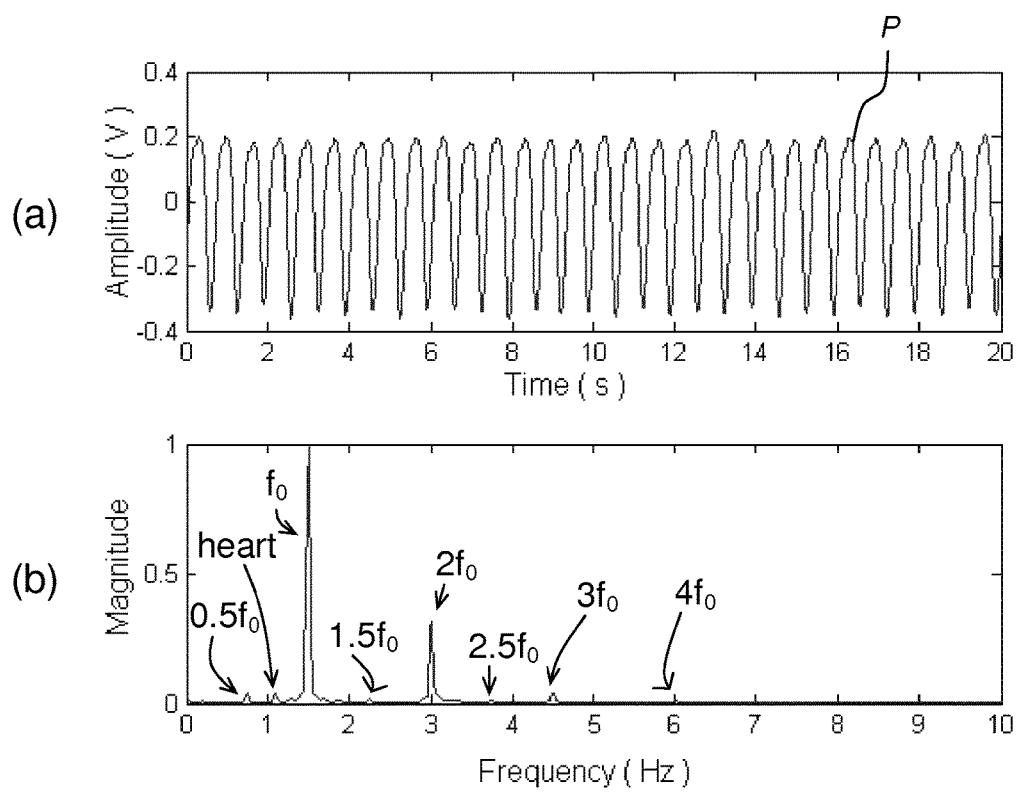
FIG. 2(a) is a plot in the time domain of a pressure signal containing both pump pulses and heart pulses.
FIG. 2(b) is a plot of the corresponding signal in the frequency domain.
Figure 3A:
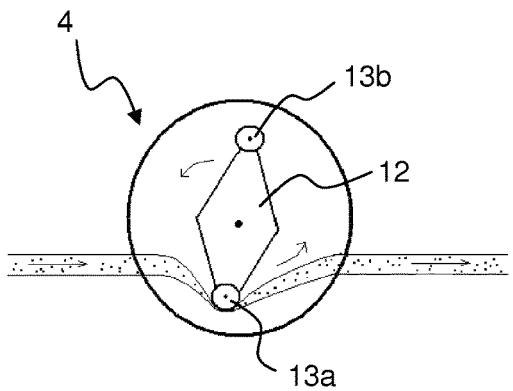
FIG. 3(a) is a side view of a rotor of a peristaltic pump.
Figure 3B:
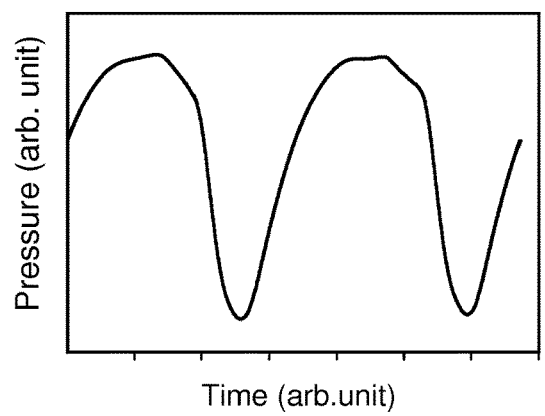
FIG. 3(b) is a plot of pressure pulses generated during a full rotation of the rotor in FIG. 3(a), as measured by a pressure sensor in the extracorporeal blood processing apparatus of FIG. 1.

FIG. 2(a) shows an example of a time-resolved pressure signal P acquired from sensor 6b in FIG. 1, and FIG. 2(b) shows the corresponding spectral density, i.e. signal energy as a function of frequency. The spectral density reveals that the pressure signal P contains frequency components that emanate from and are given by the design of the blood pump 4. As seen, the frequency components are a set of harmonic frequencies $0.5f_0$, $f_0$, $1.5f_0$, $2f_0$, etc. In the illustrated example, the blood pump 4 is a rotary peristaltic pump of the type indicated in FIG. 3(a), and the frequency components are governed by the revolution of the rotor 12 and the engagement of the rollers 13a, 13b with the tube segment. The dominating frequency $f_0$ is the pumping frequency, i.e. the frequency of pump strokes, with each pump stroke being generated by the engagement of one of the rollers 13a, 13b with the tube segment. FIG. 3(b) illustrates the pressure pulsations ("pump pulses") in the pressure signal that originate exclusively from the pump 4 during one revolution of the rotor 12. Thus, the pump pulses in FIG. 3(b) represent the pressure waves that are generated by the rollers 13a, 13b engaging the tube segment during a full rotor revolution. Returning to FIGS. 2(a)-2(b), the pressure signal P also includes pressure pulsations ("heart pulses") that originate from the beating of the heart in the patient. In this example, the heart pulses are much weaker than the pump pulses and are difficult to detect in the pressure signal P, which is dominated by the pump pulses. Generally, the pressure signal P may contain pressure pulses from any physiological pulse generator PH (FIG. 1), periodic or non-periodic, in the patient, including reflexes, voluntary muscle contractions, non-voluntary muscle contractions, the heart, the breathing system, the autonomous system for blood pressure regulation and the autonomous system for body temperature regulation. In a further alternative, the pressure signal P may contain pressure pulses from a dedicated pulse generator attached to the patient. In the following, pressure pulses originating from the patient are collectively denoted "patient pulses".

Returning to the specific example in FIG. 1, a monitoring or surveillance device 7 is connected to the pressure sensors 6a, 6b by a respective transmission line. In the following, the pressure sensors 6a, 6b are denoted "arterial pressure sensor" and "venous pressure sensor", respectively, and generate an arterial pressure signal and a venous pressure signal. The device 7 is operable to acquire and process at least one of the pressure signals from the arterial and venous pressure sensors 6a, 6b for the purpose of detecting a disruption of the fluid connection between the EC circuit 1 and the cardiovascular system of the subject. The disruption corresponds to a disconnection of the EC circuit 1 from the cardiovascular system and may be caused, e.g., by a dislodgement of one or both of the access devices 2', 2" from the vascular access 3, a rupture of a blood line, or a disconnection of a connector (not shown) which may be installed between the respective access device 2', 2" and the blood lines. As explained in the Background section, it is of particular interest to detect a disruption downstream of the blood pump 4 (commonly referred to as VND), since this may cause the subject to be drained of blood. However, it may also be relevant to detect a disruption upstream of the blood pump 4, to prevent that the EC circuit 1 pumps air into the cardiovascular system of the subject.

The device 7 operates based on the principle that the patient pulses will decrease in magnitude, or even disappear completely, in one or both of the venous and arterial pressure signals if the fluid connection is disrupted. A disruption downstream of the venous pressure sensor 6b causes the magnitude of the patient pulses to decrease in the venous pressure signal. Correspondingly, a disruption upstream of the arterial pressure sensor 6a causes the magnitude of the patient pulses to decrease in the arterial pressure signal. In certain installations, the pressure waves that originate from the patient and propagate into the EC circuit 1 may be significantly attenuated by the blood pump 4 and/or the blood processing unit 5. This may cause the patient pulses to effectively disappear from the venous pressure signal upon a venous-side disruption and from the arterial pressure signal upon an arterial-side disruption. For example, the blood pump 4 is commonly a peristaltic pump which is known to effectively block transmission of such pressure waves. The device 7 is thus configured to continuously acquire at least one of the pressure signals from the sensors 6a, 6b, compute a monitoring parameter which is responsive to the patient pulses, e.g. the magnitude of the patient pulses, and evaluate the monitoring parameter for detection of a disruption. When detecting a (potential) disruption, the device 7 may issue an alarm or warning signal and/or alert a control system of the EC circuit 1 to take appropriate action. Embodiments of the invention may e.g. be implemented by software instructions that are supplied on a computer-readable medium for execution by a processor 8 in conjunction with an electronic memory 9 in the device 7.

Figure 4:
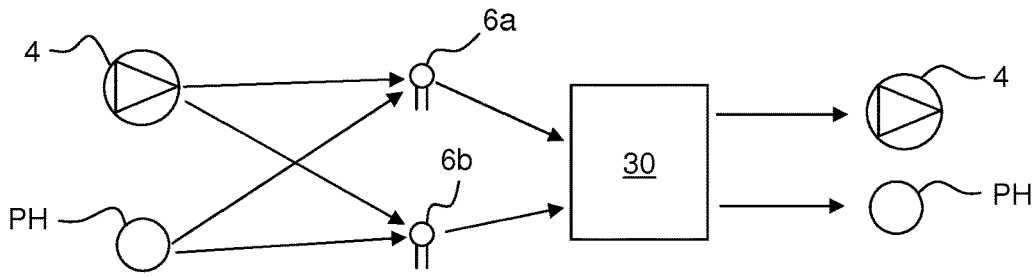
FIG. 4 illustrates a principle of a source separation technique applied to the apparatus in FIG. 1.

Embodiments of the device 7 are based on the insight that a source separation algorithm may be utilized to obtain a monitoring parameter that is responsive to the patient pulses. Source separation is a mathematical method designed to separate a set of source signals from a set of mixed signals. FIG. 4 shows a generalized example for the setup in FIG. 1. When the fluid connection is intact, each of the pressure sensors 6a, 6b receives pressure waves from the blood pump 4, acting as a first source, and a physiological pulse generator PH in the patient, acting as a second source. Thereby, each of the venous and arterial pressure signals includes an (approximately) linear mix of pump pulses and patient pulses, and the venous and arterial pressure signals are correlated. A source separation algorithm, designated by 30, may be applied to the pressure signals so as to generate a first source signal representing the operation of the pump 4 and a second source signal representing the operation of the physiological pulse generator PH. Mathematically, the source separation aims at finding the matrix S in the matrix relation X=B·S, where X contains signal vectors for the pressure recordings by the sensors 6a, 6b, S contains the unknown source signals to be separated, and B is an unknown mixing matrix.

In principle, the device 7 may implement any source separation technique to operate on the signal vectors so as to generate the source signals. However, the purpose of utilizing source separation is not to separate and reproduce the source signals per se, but rather to identify a change in the patient pulses as detected by the pressure sensors in the EC circuit 1, preferably in a robust and processing-efficient way. The present Applicant has focused on source separation techniques that involve computation of eigenvectors and/or eigenvalues, based on the matrix X of signal vectors, as part of the process of separating the source signals. It has surprisingly been found that the patient pulses are reflected among such eigenvectors and/or eigenvalues, irrespective of whether the eigenvectors are a true representation of source signals or not. An attractive property of basing the monitoring parameter on eigenvectors and/or eigenvalues is that there are many numerically stable and processing-efficient techniques for computing eigenvectors and eigenvalues. Thus, it is possible to apply well-established computation methods, possibly without requiring a full implementation of the source separation technique since only eigenvectors/eigenvalues need to be computed.

There are a number of different source separation techniques that may involve computation of eigenvectors and eigenvalues associated with the signal vectors, including but not limited to Principal Component Analysis (PCA), Independent Component Analysis (ICA), Factor Analysis, Canonical Correlation Analysis (CCA) and Common Spatial Pattern (CSP).

Figure 5:
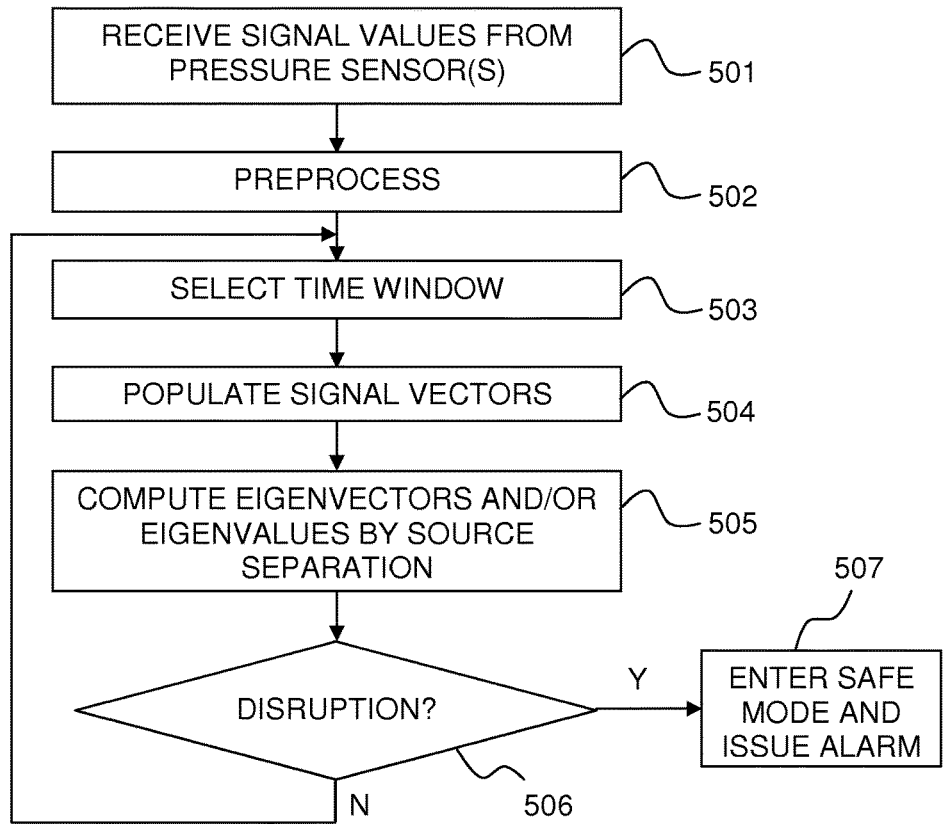
FIG. 5 is a flow chart of a monitoring method applying source separation.

FIG. 5 illustrates an embodiment of a monitoring method involving a sequence of steps that may be implemented by the device 7 shown in FIG. 1. The method involves a step 501 that receives the pressure signals from the pressure sensors 6a, 6b, and a step 502 that pre-processes the pressure signals, e.g. for AD conversion, signal amplification, removal of offset, high frequency noise and supply voltage disturbances, etc. The removal of offset may be implemented to ensure that the pre-processed pressure signals have a zero mean, which may be advantageous for the subsequent computation of eigenvectors/eigenvalues. Steps 501 and 502 may operate to continuously supply pre-processed pressure values, independently of the other steps of the method. In certain embodiments, step 502 may be omitted.

The method further includes a repeating sequence of steps 503-506 that operate on a respective time window in the pressure signals that are supplied by steps 501-502, to generate and evaluate the monitoring parameter. The consecutive time windows processed by steps 503-506 may be overlapping or non-overlapping.

In one repetition of steps 503-506, step 503 first selects a time window in the pressure signals. The length of the time window is predefined. The following examples utilize a time window of 10 seconds, corresponding to 100 pressure values (for a sampling rate of 10 Hz) in each of the two pressure signals (cf. FIG. 1). Step 504 populates one signal vector for each pressure signal, such that the respective signal vector corresponds to the pressure values within the time window. Step 504 results in n signal vectors $\bar{x}_k$, each containing m signal values. The test results presented in FIGS. 7-8 below are obtained for n=2 and m=100. Step 505 processes the signal vectors $\bar{x}_k$ by the source separation algorithm so as to compute one or more eigenvectors $\bar{v}_l$ and/or one or more eigenvalues $\lambda_l$ associated with the signal vectors $\bar{x}_k$. Step 506 computes the monitoring parameter as a function of the one or more eigenvectors $\bar{v}_l$ and/or the one or more eigenvalues $\lambda_l$, and evaluates the monitoring parameter for detection of a disruption of the fluid connection, e.g. by identifying a change to the monitoring parameter over time or by comparing the monitoring parameter to a threshold value. If the evaluation indicates a disruption, step 507 is invoked to cause the blood processing apparatus to enter a safe mode of operation and/or to issue an alarm. Otherwise, the method returns to step 503.

As an alternative to processing the pressure signals in step 502 so that they have a zero mean, step 505 may include an initial sub-step that adjusts the signal values of the signal vectors $\bar{x}_k$ to a zero mean before they are processed by the source separation algorithm. This sub-step may involve computing a mean value for the respective signal vector $\bar{x}_k$ and subtracting this mean value from the signal values in the signal vector $\bar{x}_k$. Alternatively, a single mean value may be computed for all signal vectors $\bar{x}_k$ or for the pressure values within the time window, and subtracted.

Figure 6:
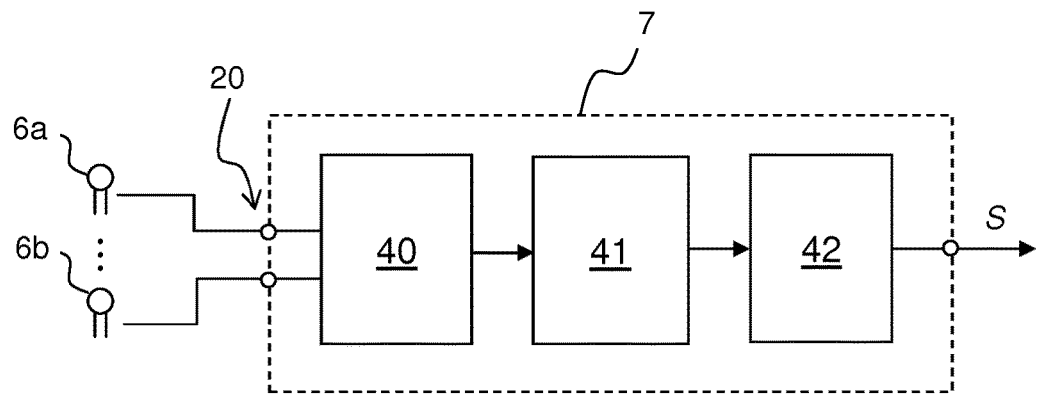
FIG. 6 is a block diagram of a monitoring device applying source separation to a combination of pressure signals for disruption detection.

FIG. 6 shows an embodiment of the device 7 that implements the method of FIG. 5. The device 7 contains an input interface 20 for connection to the pressure sensors 6a, 6b. An extraction module 40 is connected to the input interface 20 to receive the pressure signals (step 501). The extraction module 40 is further configured to pre-process the pressure signals (step 502), extract pressure values from the pressure signals (step 503) and populate the signal vectors $\bar{x}_k$ based on the extracted pressure values, one signal vector for each pressure signal (step 504). A source separation module 41 is configured to process the signal vectors $\bar{x}_k$ by the source separation algorithm, resulting in the eigenvector(s) $\bar{v}_j$ and/or the eigenvalue(s) $\lambda_j$ associated with the signal vectors $\bar{x}_k$ (step 505). A detection module 42 is configured to compute and evaluate the monitoring parameter (step 506), and to output a fault signal S if a disruption is detected when evaluating the monitoring parameter (step 507).

Below follows more detailed examples on the use of PCA and ICA as the source separation algorithm in the embodiments of FIGS. 5-6. PCA is a statistical procedure that uses a transformation to convert a set of observations of correlated variables into a set of values of linearly uncorrelated variables called "principal components". The number of principal components is less than or equal to the number of original variables. The transformation is defined in such a way that the first principal component has the largest possible variance, i.e. accounts for as much of the variability in the data as possible, and each succeeding component in turn has the highest variance possible under the constraint that it is orthogonal to (i.e., uncorrelated with) the preceding components. Thus, PCA results in a number of principal components for the set of observations, and may also result in a variance for each principal component. Theoretically, PCA involves applying an orthogonal linear transformation to a set of signal vectors which are at least partially correlated to generate a set of transformed signal vectors that are uncorrelated. It can be shown that finding the transformed signal vectors is equivalent to finding the eigenvectors of the covariance matrix for the set of signal vectors. It should be noted that ICA is similar to PCA and also involves finding the eigenvectors of the covariance matrix for the set of signal vectors, with the further constraint that the eigenvectors should not only be uncorrelated but also independent.

To further exemplify PCA/ICA, consider having n signal vectors $\bar{x}_k$, each containing m signal values:

$$\bar{x}_k = \begin{bmatrix} x_k(1) \\ x_k(2) \\ \vdots \\ x_k(m) \end{bmatrix} \quad k = 1, 2, \ldots, n$$

The covariance matrix may be estimated for the signal vectors $\bar{x}_k$ by forming a data matrix X, in which the signal vectors are arranged as rows $$X = \begin{bmatrix} \bar{x}_1^T \\ \bar{x}_2^T \\ \vdots \\ \bar{x}_n^T \end{bmatrix}$$

and by evaluating the matrix operation $X^T \cdot X$, where superscript T indicates a transpose. The estimated covariance matrix $\hat{C}$ is given by $f(X^T \cdot X)$, where $f$ is any suitable linear function. For example, the function $f$ may be designed to normalize $X^T \cdot X$ in proportion to the number of signal vectors, e.g. through a division by n or n−1. The data matrix X has size n×m (number of rows times number of columns), and the estimated covariance matrix $\hat{C}$ contains m×m estimated covariance values. It can be noted that $X^T \cdot X$ corresponds to the element-wise sum of the auto-correlations for the respective signal vector $\bar{x}_k$, given by $$\sum_{k=1}^{N} \bar{x}_k \cdot \bar{x}_k^T.$$

This type of estimated covariance matrix $\hat{C}$ enables computation of a maximum of n eigenvectors (if n<m) or m (if m<n) having a respective length of m signal values. In an alternative implementation, the data matrix X is formed by arranging the signal vectors $\bar{x}_k$ as columns: $X = [\bar{x}_1 \bar{x}_2 \ldots \bar{x}_n]$, where X has size m×n. The estimated covariance matrix $\hat{C}$ may still be given by $f(X^T \cdot X)$ and has size n×n. This type of estimated covariance matrix $\hat{C}$ enables computation of a maximum of n (if n<m) or m (if m<n) eigenvectors having a respective length of n signal values. It should be noted that while the foregoing techniques of defining the estimated covariance matrix $\hat{C}$ are believed to be straightforward and sufficiently accurate, there are more advanced techniques that may be employed, including regularized or shrinkage estimators.

Source separation by PCA/ICA involves computing a set of eigenvectors and eigenvalues for the estimated covariance matrix $\hat{C}$. The eigenvectors and eigenvalues may be computed using any known technique, e.g. by determining the matrix V of eigenvectors which diagonalizes the estimated covariance matrix $\hat{C}$: $V^{-1} \cdot \hat{C} \cdot V = D$, where D is the diagonal matrix of eigenvalues for the estimated covariance matrix $\hat{C}$. The column vectors of the matrix V represent the eigenvectors of the estimated covariance matrix $\hat{C}$. The eigenvalues and eigenvectors are ordered and paired, i.e. the jth eigenvalue in D corresponds to the jth eigenvector in V. In another example, which obviates the need to explicitly calculate the estimated covariance matrix $\hat{C}$, the eigenvectors and eigenvalues are computed by the singular value decomposition (SVD) of X, as is well-known in the art.

Figure 7:
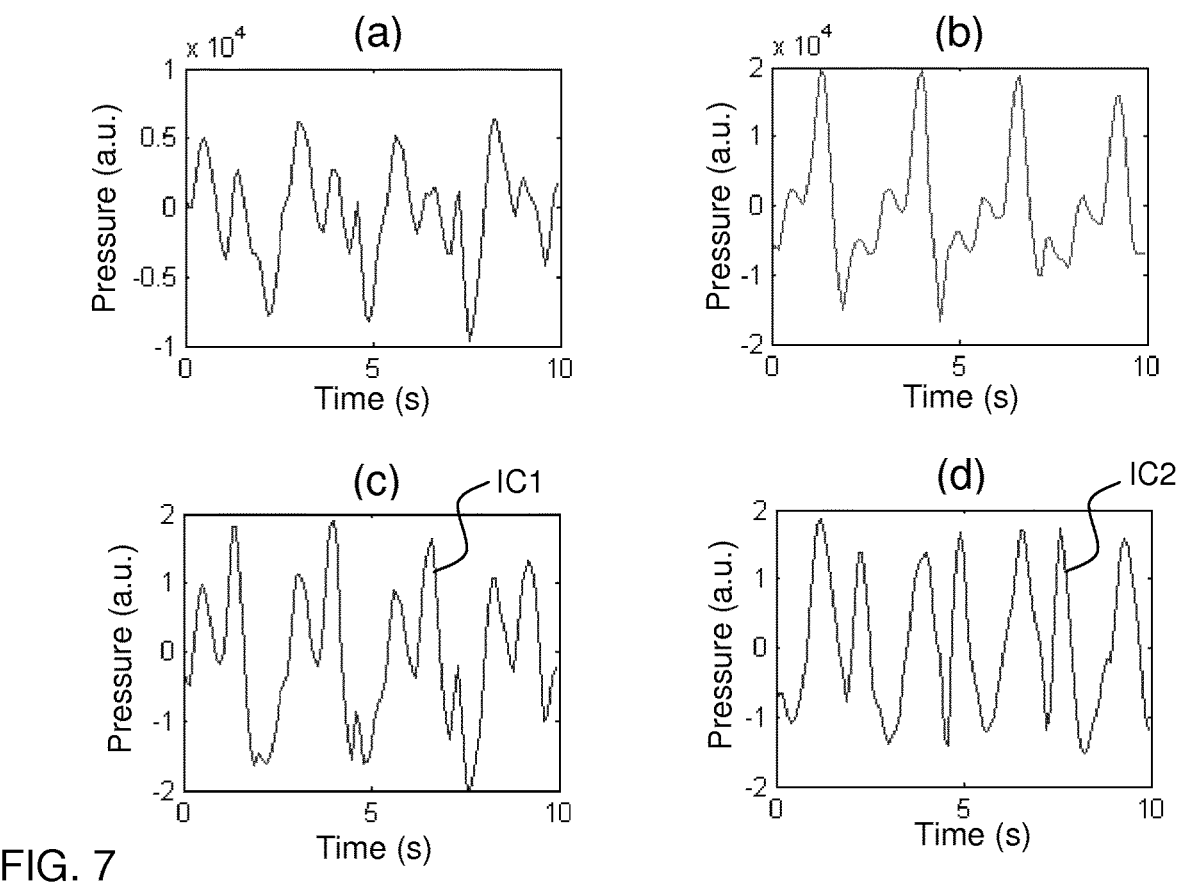
FIGS. 7(a)-(b) are plots of venous and arterial pressure signals before VND.
FIGS. 7(c)-(d) are plots of corresponding computed eigenvectors before VND.
Figure 8:
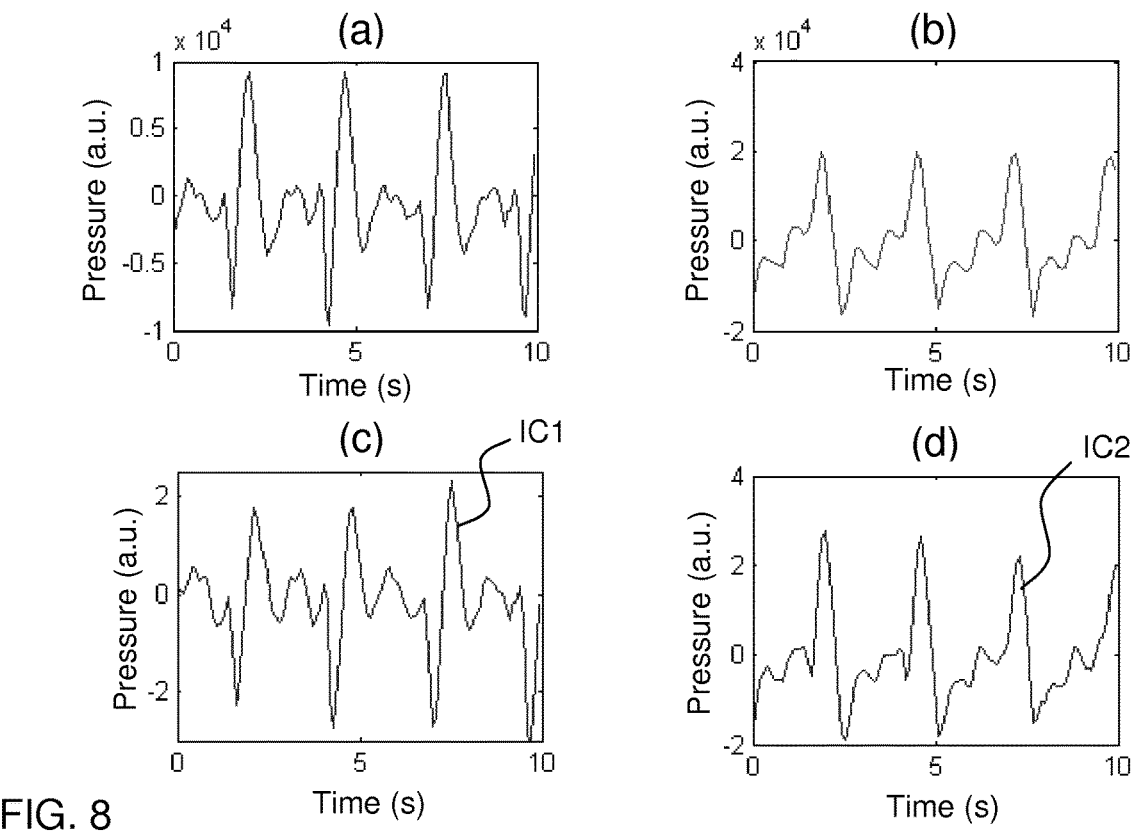
FIGS. 8(a)-(d) are plots of the data in FIGS. 7(a)-(d) after VND.

FIGS. 7-8 are signal plots that illustrate the effectiveness of the technique described in the foregoing. The signal plots represent a respective time window in a venous pressure signal (FIG. 7(a)) and an arterial pressure signal (FIG. 7(b)), which are acquired when the fluid connection is intact (cf. FIG. 1). Each pressure signal includes both pump pulses and heart pulses, but the heart pulses are difficult to identify since the pump pulses dominate the pressure signals. Although not shown, it is to be understood that the pressure signal may include further patient pulses, e.g. from the breathing system, and/or further interference pulses, e.g. from valves or other pumps in the EC circuit 1. The signal plots in FIGS.

7(c)-(d) show the independent components IC1, IC2 generated by ICA for the pressure signal in FIGS. 7(a)-(b). The independent components IC1, IC2 correspond to two eigenvectors $\bar{v}_1$, $\bar{v}_2$ obtained by operating an ICA algorithm on signal vectors $\bar{x}_1$, $\bar{x}_2$ populated by the pressure values in FIG. 7(a) and FIG. 7(b), respectively. FIGS. 8(a)-(b) show the venous and arterial pressure signals, respectively, when the venous access device 2" has been detached from the vascular access 3. FIGS. 8(c)-(d) show the independent components IC1, IC2 generated by ICA for the pressure signals in FIGS. 8(a)-(b).

It is seen that the components (eigenvectors) IC1, IC2 change significantly when the venous access device 2" is detached from the vascular access 3. Clearly, it is possible to detect a disruption based on the eigenvectors calculated by ICA. It may also be noted that, for an intact fluid connection, one component mainly represents the pump pulses (IC1 in FIG. 7(c)) and the other mainly represents the heart pulses (IC2 in FIG. 7(d)). After a disruption of the fluid connection, the components rather represent the pump pulses in the respective pressure signal (compare FIG. 8(a) to FIG. 8(c), and FIG. 8(b) to FIG. 8(d)). Although not illustrated, it may also possible to detect a disruption based on the eigenvalues that are associated with the eigenvectors. Examples of monitoring parameters, computed as a function of the eigenvectors/eigenvalues, are given further below with reference to another embodiment presented in FIGS. 9-13. These monitoring parameters are also applicable to the embodiment presented above in relation to FIGS. 5-8.

For increased certainty of detection, it may be desirable to increase the number of eigenvectors and/or eigenvalues produced by the source separation algorithm. This may be achieved by acquiring and processing a larger number pressure signals, i.e. a larger number of signal vectors. For example, it is not uncommon for a blood treatment apparatus to include a pressure sensor between the blood pump 4 and the blood processing unit 5, as well as a pressure sensor in a circuit (not shown) for pumping a treatment fluid (e.g. a dialysis fluid) through the blood processing unit 5 (FIG. 1). However, there are blood treatment apparatuses that have only a few pressure sensors, or even only one pressure sensor. It would be desirable to increase the number of eigenvectors/eigenvalues beyond the number of pressure sensors. It would also be desirable to increase the specificity of the detection, i.e. to be able to discriminate between a disruption on the venous side and a disruption on the arterial side, which may be difficult to achieve with the above-described detection technique.

Figure 9:
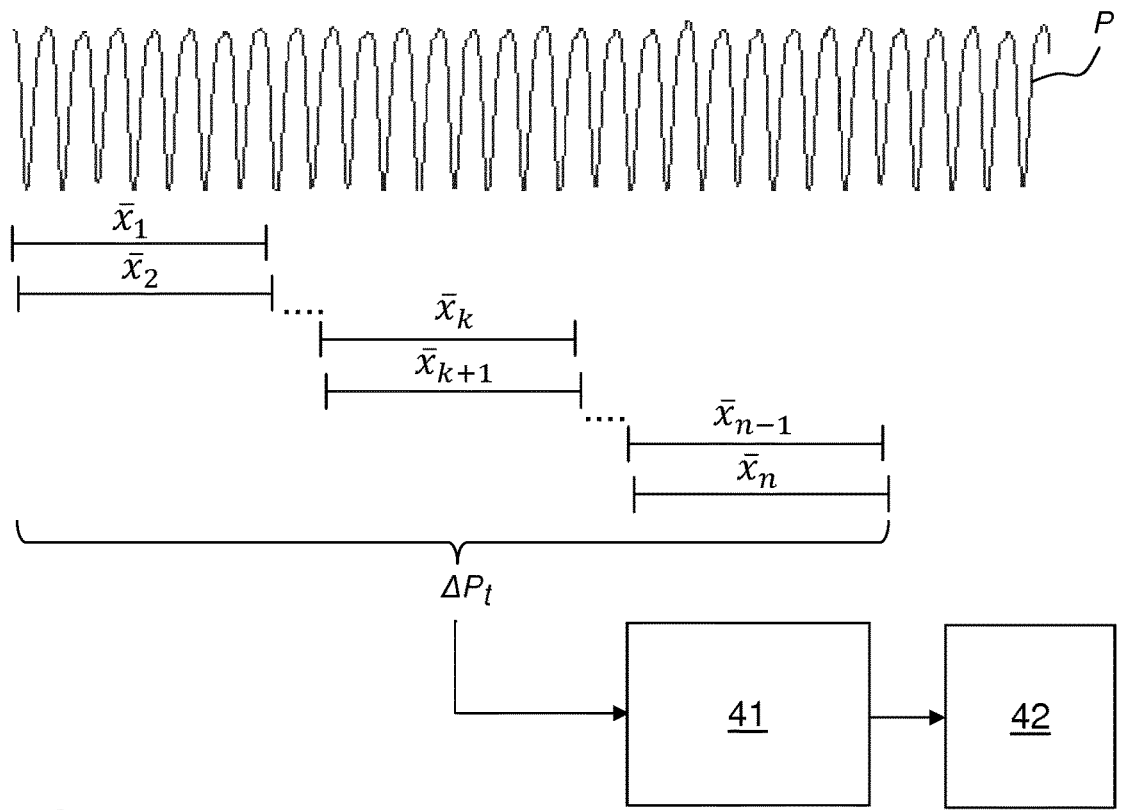
FIG. 9 illustrates a technique for populating signal vectors from a single pressure signal.

It has surprisingly been found that an increase in the number of eigenvectors/eigenvalues may be achieved by populating the signal vectors by time-shifted signal segments in one at the same pressure signal. This concept is illustrated in FIG. 9, in which a number of n signal vectors, each designated by $\bar{x}_k$, k=1, . . . , n, are populated to correspond to a predefined set of n time-shifted and mutually overlapping signal segments within a time window $\Delta P_t$ in a pressure signal P. These signal vectors) $\bar{x}_k$ are correlated, since the same pressure pulses show up in all or at least part of the segments, depending on the length of the segments. Preferably, each segment has a sufficient length to contain a plurality of pump pulses, when present in the pressure signal. When such a set of signal vectors is processed by source separation, it may be possible to compute n different eigenvectors, if desired. Each eigenvector will be dominated by a frequency that represents one of the available sources, e.g. the pump, the heart or the breathing system. This concept may also increase the specificity of the disruption detection, since the resulting eigenvectors/eigenvalues will represent the pulsations in the pressure signal. Changes in the pressure signal will affect and be detectable by the eigenvectors/eigenvalues. It is currently believed that the concept of using time-shifted segments is best suited when the patient pulses that are observed for detection of the disruption occur periodically in the pressure signal.

Figure 10A:
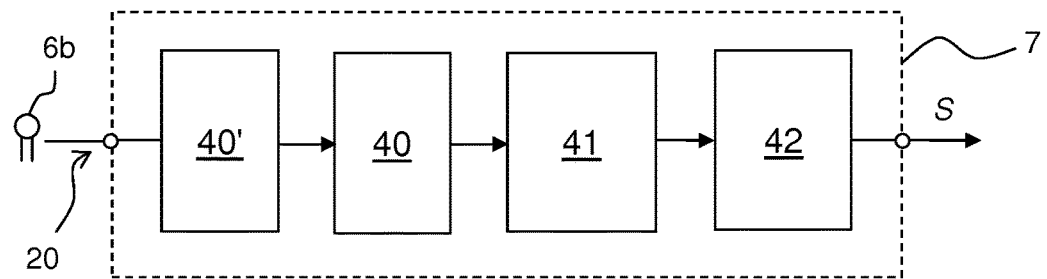
FIGS. 10(a)-(b) are block diagrams of monitoring devices applying source separation for disruption detection.

FIG. 10(a) illustrates an embodiment based on this concept. The monitoring device 7 in FIG. 10(a) includes the same modules 40-42 as the device in FIG. 6, but the extraction module 40 is configured to populate the set of signal vectors by extracted pressure values from a single pressure signal, in this example the venous pressure signal from sensor 6b. The source separation module 41 and the detection module 42 may be identical to the modules 41, 42 in FIG. 6, although variants will be presented further below. In the example of FIG. 10(a), the device 7 includes a dedicated filtering module 40', which is arranged to receive the pressure signal from the input interface 20 and is operable to filter the pressure signal P for suppression of the pump pulses, preferably such that the pump pulses are smaller in magnitude (amplitude) than the heart pulses. The filtering module 40' need not be a separate module, as shown, but may be integrated as part of the extraction module 40. The pre-filtering ensures that the most significant eigenvector(s) produced by module 41 originate from the heart, which may facilitate the disruption detection by module 42.

The device in FIG. 10(a) may implement the monitoring method shown in FIG. 5. Compared to the description of FIG. 5 given above with reference to FIG. 1, steps 501, 503 and 505 are identical, whereas step 502 additionally includes the pre-filtering by module 40'. Any known filtering technique may be used, e.g. any one of the techniques disclosed in WO97/10013, US2005/0010118, WO2009/156175, WO2010/149726, WO2010/149726, WO2013/000777, WO2014/009111, and WO2015/032948. The requirements on module 40' are relatively modest, since its purpose is merely to suppress the pump pulses. In each repetition, step 503 selects a time window $\Delta P_t$ in the pressure signal P (FIG. 9). Step 504 populates the signal vectors $\bar{x}_k$ such that each signal vector corresponds to a respective signal segment within the time window $\Delta P_t$ (FIG. 9). In all examples given herein, it is assumed that the signal vectors are populated by the respective signal segment, i.e. the values $x_k(i)$ of the respective signal vector $\bar{x}_k$ are directly given by the pressure values in the signal segment. However, other alternatives are conceivable. For example, each signal value $x_k(i)$ may be given by grouping and combining pressure values in the signal segment, e.g. as a sum, a product or an average of a number of consecutive pressure values. In the following examples, each signal vector $\bar{x}_k$ corresponds to a signal segment of 12 seconds in the pressure signal, and thus m=120 (for a sampling rate of 10 Hz), and consecutive signal segments are displaced by one data sample within the time window $\Delta P_t$. Thus, the number of signal vectors $\bar{x}_k$ is 81 (=n), and each signal vector $\bar{x}_k$ is given by:

$$\bar{x}_k = \begin{bmatrix} P(k) \\ P(k+1) \\ \vdots \\ P(k+m-1) \end{bmatrix} k = 1, 2, \ldots, n$$

where P(k) denotes the pressure value at position k within the time window.

Step 505 computes the eigenvectors and/or the eigenvalues for the estimated covariance matrix $\hat{C}$, which may be given by $f(X^TX)$ as described above. It should be noted that step 505 need not compute all possible eigenvectors/eigenvalues for the estimated covariance matrix $\hat{C}$. The number of eigenvectors to be computed may be predefined, e.g. given by previous testing and/or simulation. The computed eigenvalues may optionally be normalized by any suitable value, e.g. given by the total sum of eigenvalues. In the following, the non-normalized eigenvalues are denoted "absolute eigenvalues", and the eigenvalues normalized by the total sum are denoted "relative eigenvalues". Depending on monitoring parameter, step 505 may compute only eigenvectors, only eigenvalues, or both eigenvectors and eigenvalues.

Figure 11A:
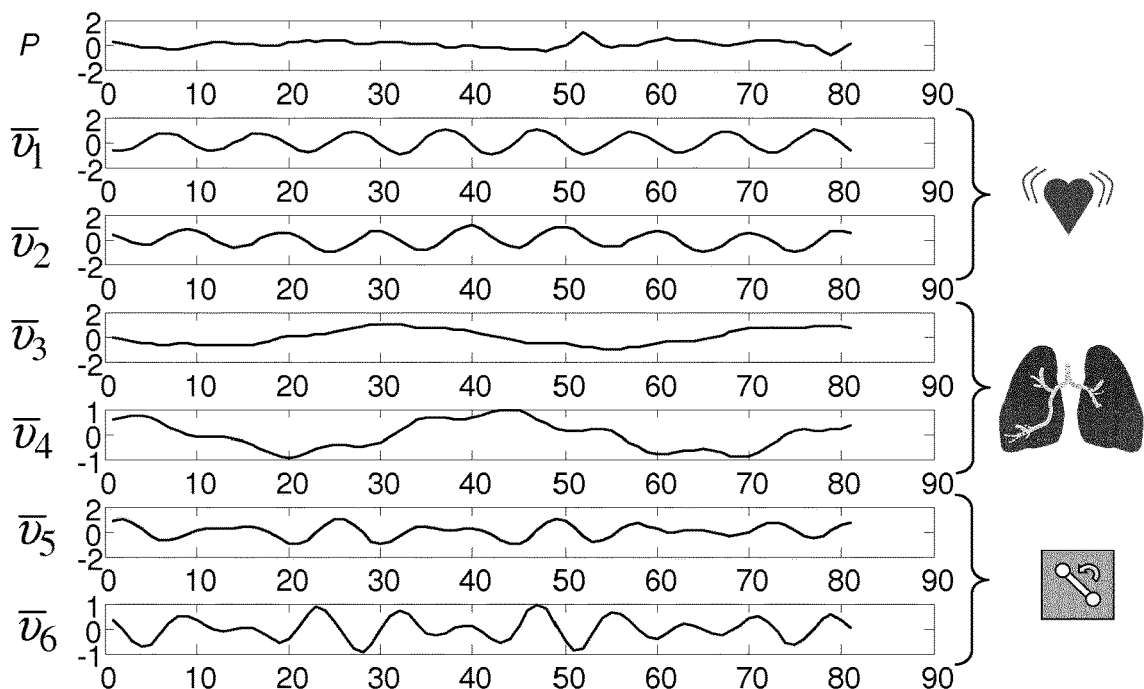
FIGS. 11(a)-(b) illustrate an ordered set of eigenvectors computed for a venous pressure signal, before VND and after VND, respectively.

As an example, FIG. 11(a) illustrates a portion of the venous pressure signal P and the six most significant eigenvectors $\bar{v}_1, \ldots, \bar{v}_6$ computed by PCA for 81 overlapping segments in the signal P while the fluid connection is intact, i.e. when both access devices 2', 2" are located in the vascular access 3. As seen, the heart pulses are barely visible in the pressure signal P. The eigenvectors are ordered by magnitude of the associated eigenvalue. The eigenvalue indicates the energy content in the respective eigenvector, and the ordering of the eigenvectors by eigenvalue therefore represents their relative importance for the appearance of the pressure signal within the time window. In the illustrated example, eigenvectors $\bar{v}_1, \bar{v}_2$ represent the heart, eigenvectors $\bar{v}_3, \bar{v}_4$ represent the breathing system, and eigenvectors $\bar{v}_5, \bar{v}_6$ represent the blood pump 4. By the pre-filtering in step 502 (module 40'), it is ensured that the eigenvectors with the largest eigenvalues represent patient pulses, provided that the pressure signal has a zero mean. If PCA processing is performed on an estimated correlation matrix $\hat{C}$ obtained from signal vectors $\bar{x}_k$ with non-zero mean, the mean is likely to be reflected in the most significant eigenvector(s).

Figure 11B:
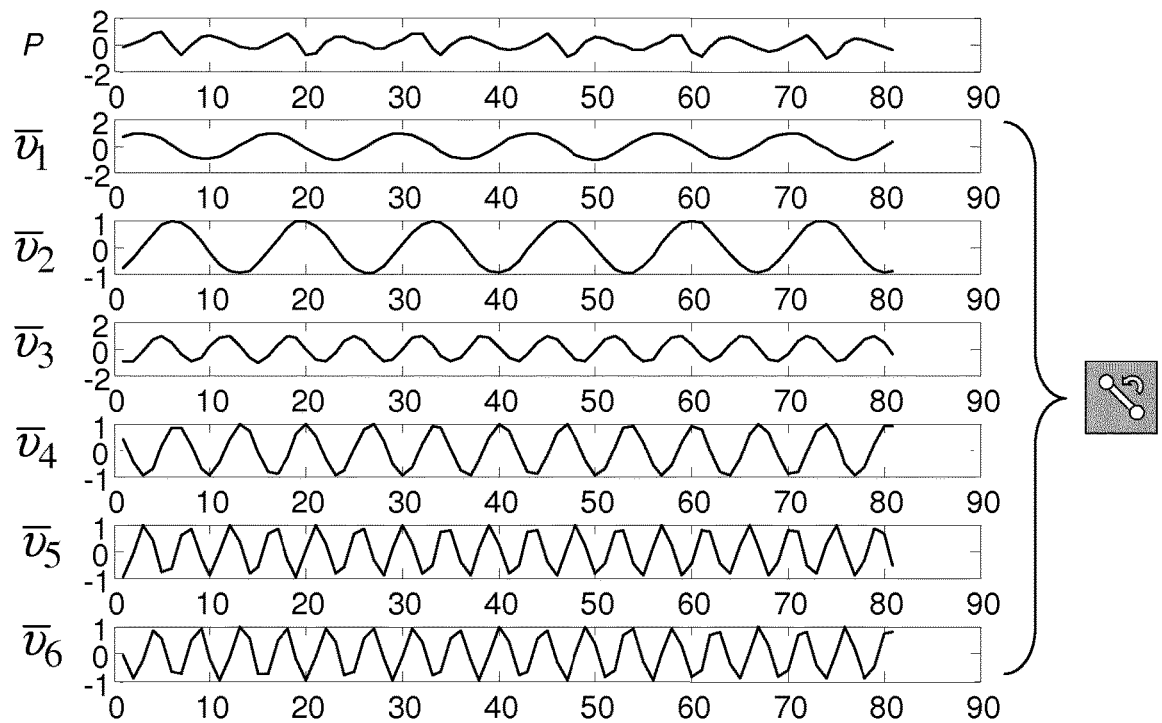

For comparison, FIG. 11(b) illustrates the venous pressure signal P and the six most significant eigenvectors $\bar{v}_1, \ldots, \bar{v}_6$ computed by PCA when the venous access device 2" is disconnected from the vascular access 3. As seen, all eigenvectors represent the pump.

Reverting to FIG. 5, the detection step 506 computes the monitoring parameter to reflect the difference between FIG. 11(a) and FIG. 11(b). It is important to understand that the correspondence between an eigenvector/eigenvalue and a specific source is not known to step 506, which merely receives a set of eigenvectors and/or eigenvalues from step 505.

Figure 12A:
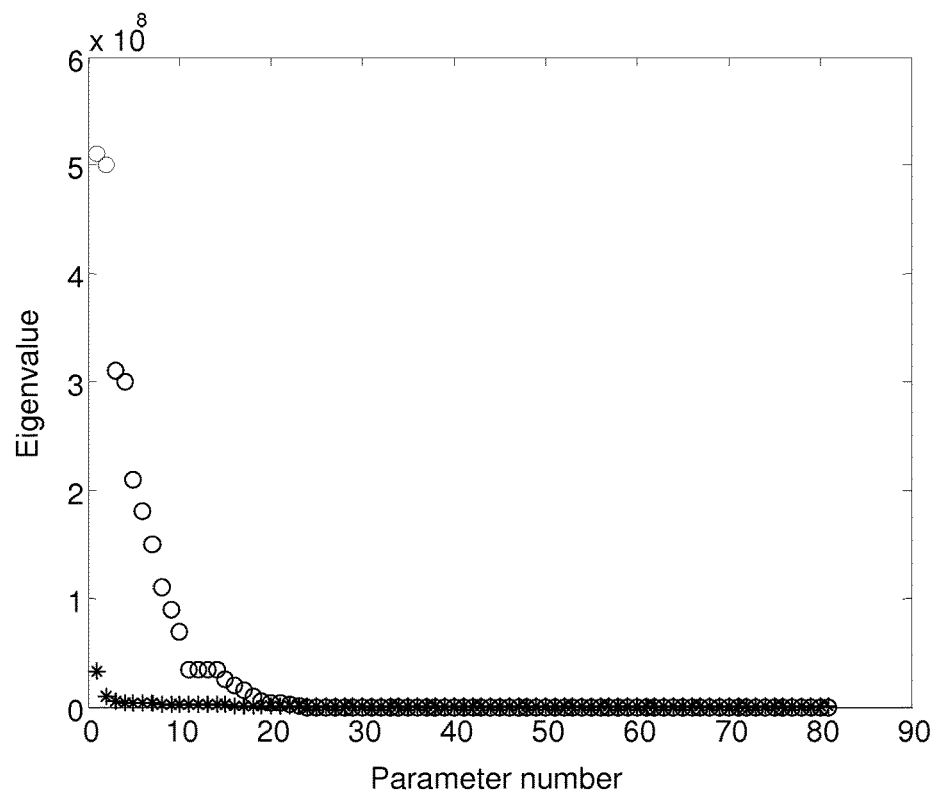
FIGS. 12(a)-(f) are distribution plots representing eigenvalues computed for a venous pressure signal.
Figure 12B:
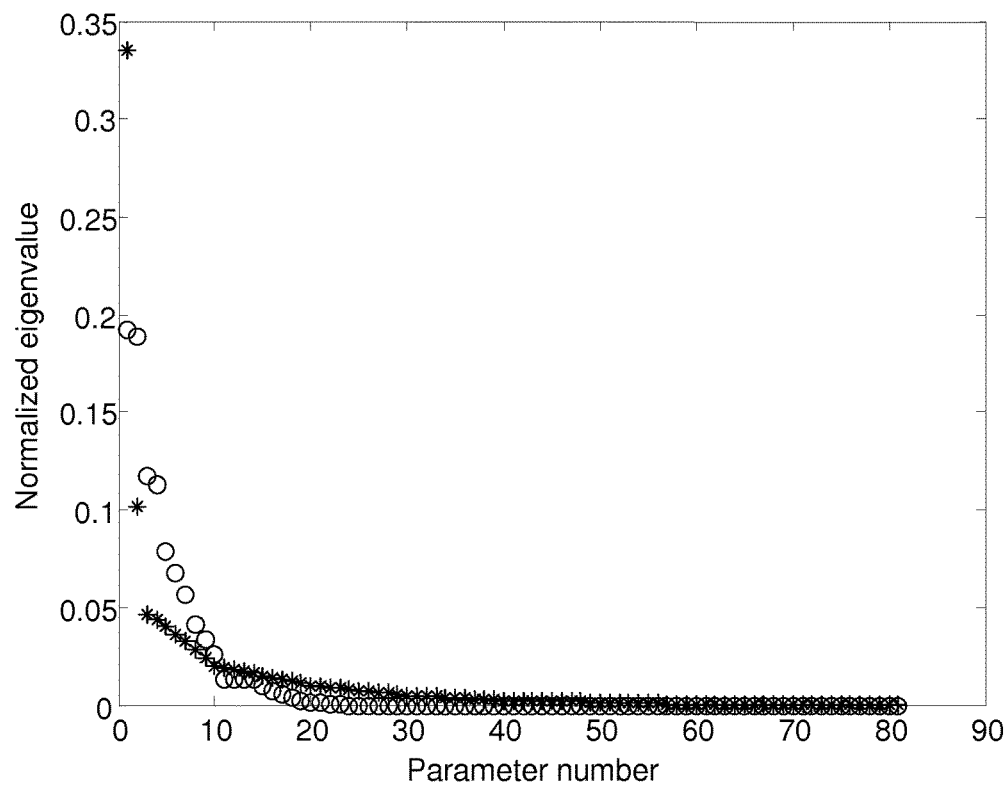
Figure 12C:
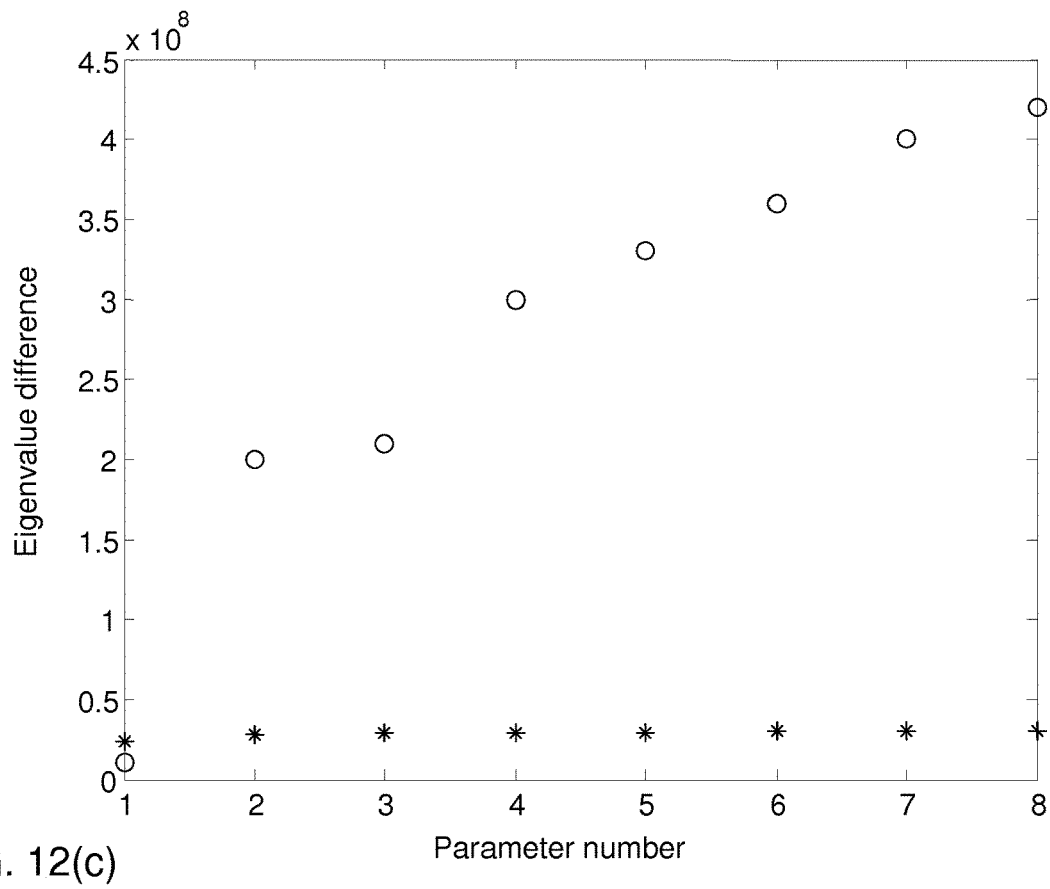
Figure 12D:
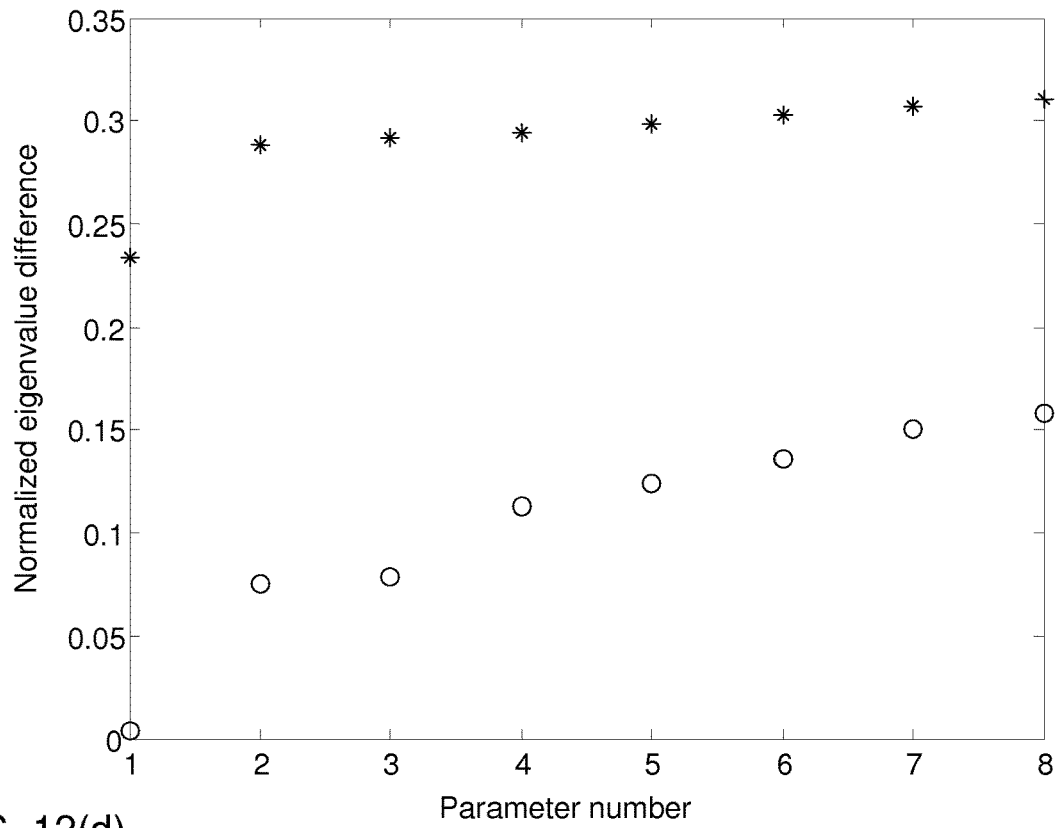
Figure 12E:
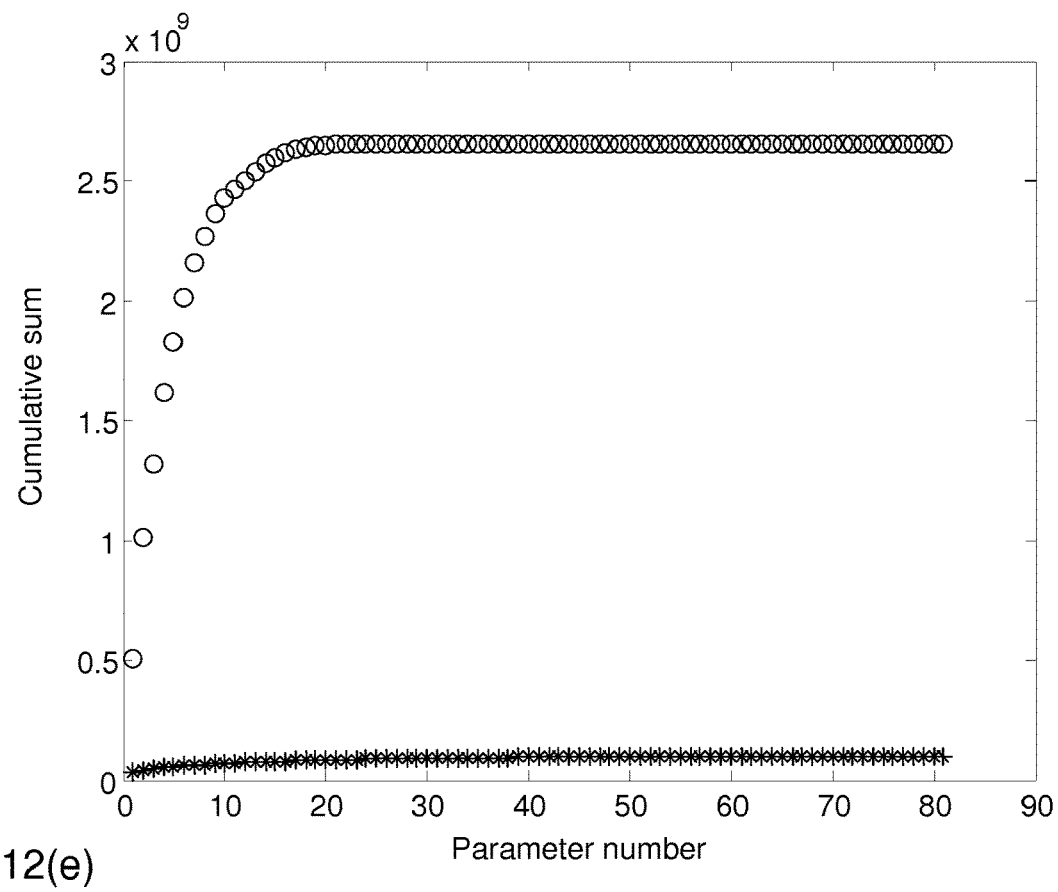
Figure 12F:
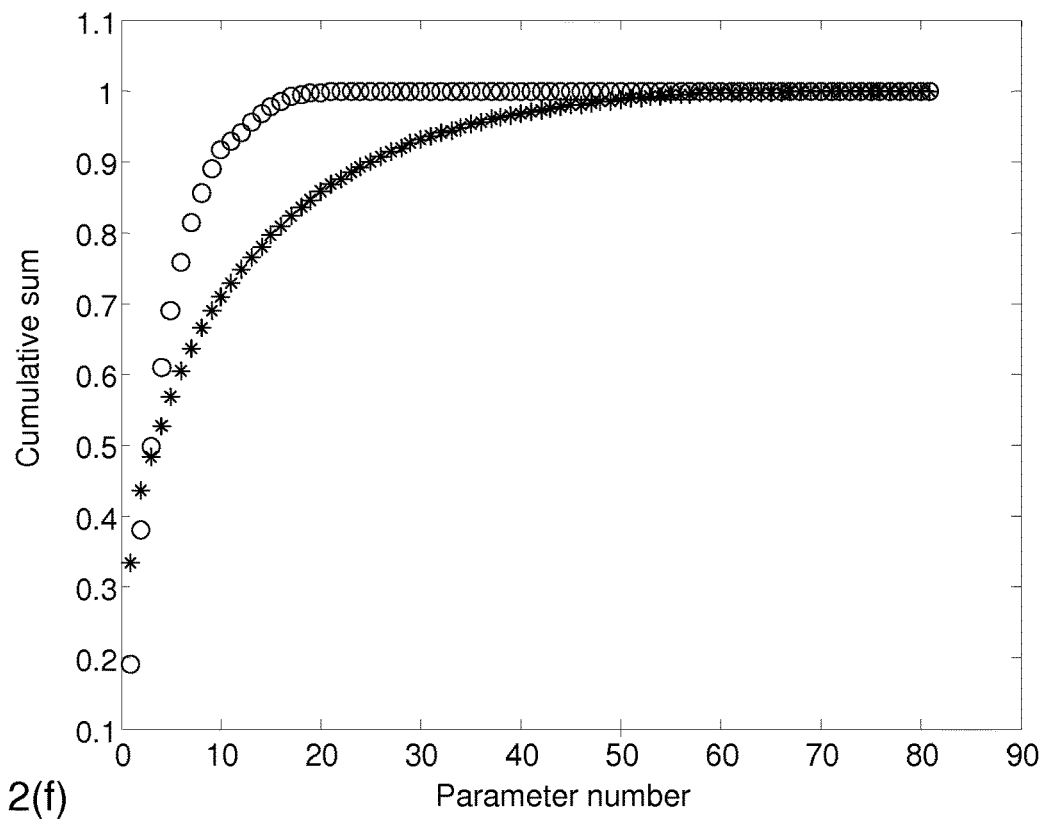

FIGS. 12(a)-(f) are plots of various parameters representing the eigenvalues that have been computed for the venous pressure signal in FIG. 9, before (open circles) and after (stars) a venous-side disruption of the fluid connection. In all plots, parameter values are arranged with decreasing eigenvalues along the abscissa. Thus, "parameter number" denotes a sequence number or order number when the parameter values are ordered by decreasing magnitude. FIG. 12(a) is a plot of absolute eigenvalues. The eigenvalues are "absolute" in the sense that they are not normalized after being computed by PCA. FIG. 12(b) is a plot of relative eigenvalues, which are "relative" in the sense that they are normalized such that the sum of all relative eigenvalues is 1. FIG. 12(c) is a plot of absolute difference values given by a difference between the respective absolute eigenvalue and the first (largest) absolute eigenvalue, for parameter numbers 2-9 in FIG. 12(a). FIG. 12(d) is a plot of relative difference values given by the difference between the respective relative eigenvalue and the first (largest) relative eigenvalue, for parameter numbers 2-9 in FIG. 12(b). FIG. 12(e) is a plot of a cumulative sum of the absolute eigenvalues in FIG. 12(a), and FIG. 12(f) is a plot of a cumulative sum of the relative eigenvalues in FIG. 12(b). The cumulative sum for parameter number m equals the sum of all parameter values with parameter numbers 1-m when the parameter values are ordered by decreasing magnitude.

Some grounds for monitoring parameters may be identified based on FIGS. 12(a)-(f). As seen, a disruption results in a change in the distribution of absolute and relative eigenvalues when ordered by magnitude. In the illustrated example, the largest absolute eigenvalues decrease in magnitude, whereas the largest relative eigenvalues increase in magnitude for some parameter numbers and decrease in magnitude for other parameter numbers. The absolute difference values decrease (for most parameter numbers) and the relative difference values increase after a disruption. The cumulative sum of absolute eigenvalues decrease. The cumulative sum of relative eigenvalues increases provided that it represents no more than the largest two quartiles of the relative eigenvalues. FIGS. 12(a)-(f) are merely given as examples and other changes are conceivable depending on implementation. However, FIGS. 12(a)-12(f) indicate that the monitoring parameter may be computed based on absolute or relative eigenvalues to represent the magnitude of at least a subset of the eigenvalues (e.g. a cumulative sum), a difference between pairs of eigenvalues for at least a subset of the eigenvalues, or a distribution of at least a subset of the eigenvalues, or any combination thereof.

Figure 13A:
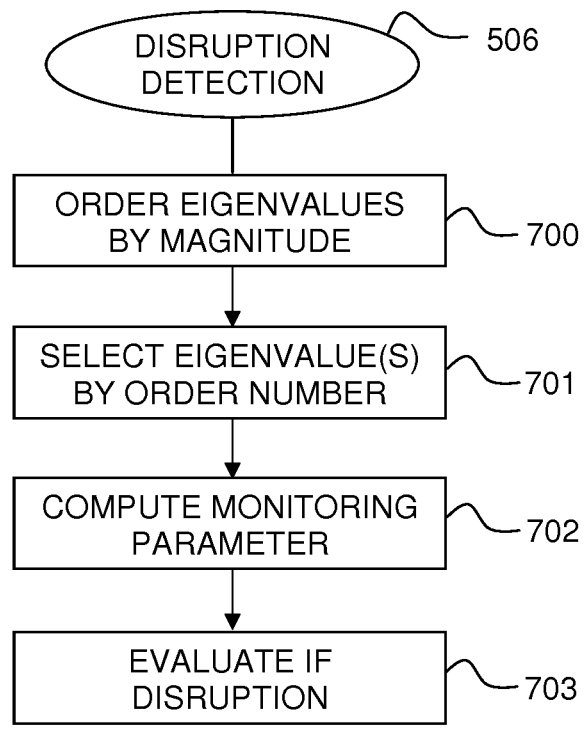
FIGS. 13(a)-(b) are flow charts of a process for disruption detection using computed eigenvalues and eigenvectors, respectively.

FIG. 13(a) shows an implementation example of step 506 in FIG. 5 when the monitoring parameter is computed to represent the eigenvalues. In step 700, the eigenvalues computed by step 505 are ordered by magnitude, in a sequence, such that each eigenvalue has an order number in the sequence. Step 701 applies a predefined rule to select a subset of the ordered eigenvalues based on their order number. Step 702 computes the monitoring parameter based on the subset of eigenvalues. In step 703, the monitoring parameter is evaluated for detection of a disruption of the fluid connection. In one example, the monitoring parameter is given by the magnitude of a single eigenvalue. In another example, the monitoring parameter is given by a magnitude of a plurality of eigenvalues, e.g. calculated as a sum, an average, a median, etc. In another example, the monitoring parameter is given by a single or accumulated difference between one or more pairs of eigenvalues. In another example, the monitoring parameter is given by the distribution of the selected eigenvalues when sorted by magnitude.

As used herein, "order by magnitude" does not imply that all of the computed eigenvalues need to be ordered in a sequence, but only that a sufficient sorting is made among the computed eigenvalues to allow the subset to be selected.

It is to be noted that step 700 and/or step 701 may be omitted. For example, step 702 may compute the monitoring parameter as the magnitude of all absolute eigenvalues (i.e., steps 700 and 701 are omitted). In another example, step 702 may compute the monitoring parameter to represent the distribution of all eigenvalues when sorted by magnitude (i.e., step 701 is omitted). It is also to be understood that more than one of the above-mentioned monitoring parameters may be computed by step 702 and evaluated by step 703.

Figure 13B:
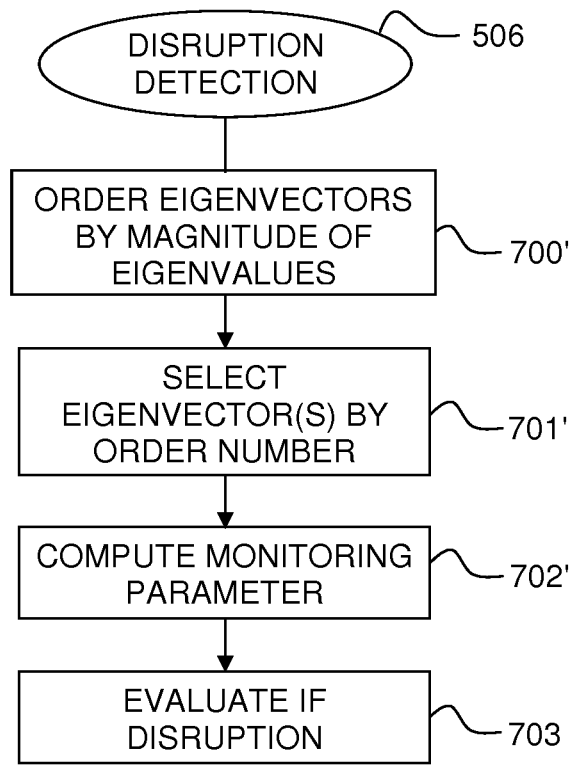

Additionally or alternatively, the monitoring parameter may be computed to represent the eigenvectors. FIG. 13(b) shows such an implementation example for step 506 in FIG. 5. Step 700' orders the eigenvectors in a sequence by the magnitude of the associated eigenvalues. Step 701' selects one or more eigenvectors by the order number of the associated eigenvector. Step 702' computes the monitoring parameter based on the selected eigenvector(s). In step 703, the monitoring parameter is evaluated for detection of a disruption of the fluid connection. In one example, the monitoring parameter represents the shape of the respective selected eigenvector. The shape may e.g. be given by computing the statistical variability of the eigenvector, e.g. given as skewness or kurtosis. In another example, the monitoring parameter is given by the dominant frequency of the selected eigenvector(s). As understood from FIGS. 11(a)-(b), a disruption changes the origin of the most significant eigenvector(s). A sudden change in frequency of these eigenvector(s) may thus indicate a disruption. Alternatively, a disruption may be identified by comparing the frequency of the selected eigenvector(s) with the frequency of the blood pump 4, if known or estimated. The frequency of the blood pump 4 may be given by a reference signal which is received by the device 7, via the input interface 20. The reference signal may indicate any one of the frequencies $0.5f_0$, $f_0$, etc. A disruption causes the frequency of the selected eigenvector(s) to have a known relation to the frequency indicated by the reference signal. The reference signal may be obtained from a tachometer associated with the pump 4 to measure the rotation speed of an element (e.g. the rotor 12) in the power transmission of the pump 4. Alternatively, the reference signal may be a control signal for the pump 4, or a pressure signal generated by a pressure sensor in the EC circuit 1, e.g. the arterial pressure signal. It is also conceivable to use the venous pressure signal, suitably before it is pre-filtered by module 40', provided that the current operating frequency of the pump can be reasonably well approximated from the pulsations in the venous pressure signal.

Figure 10B:
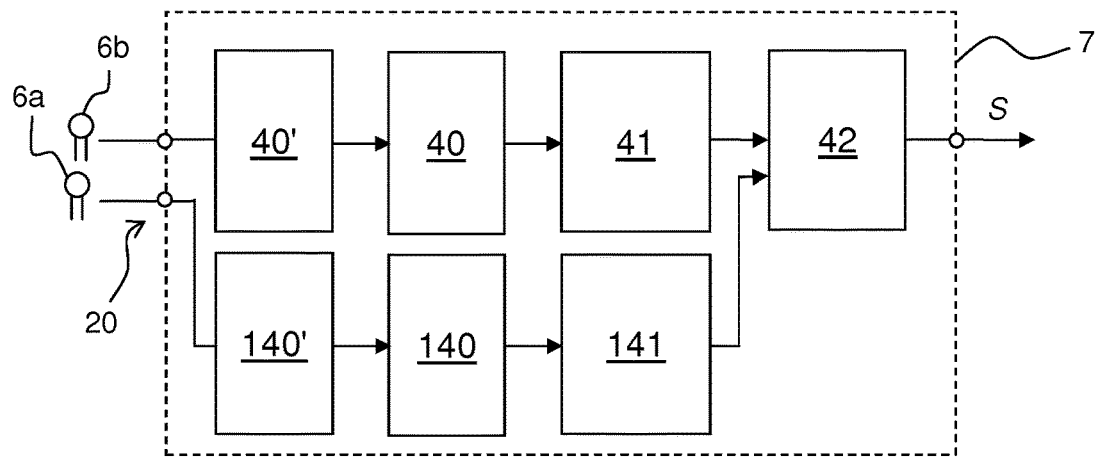
Figure 11C:
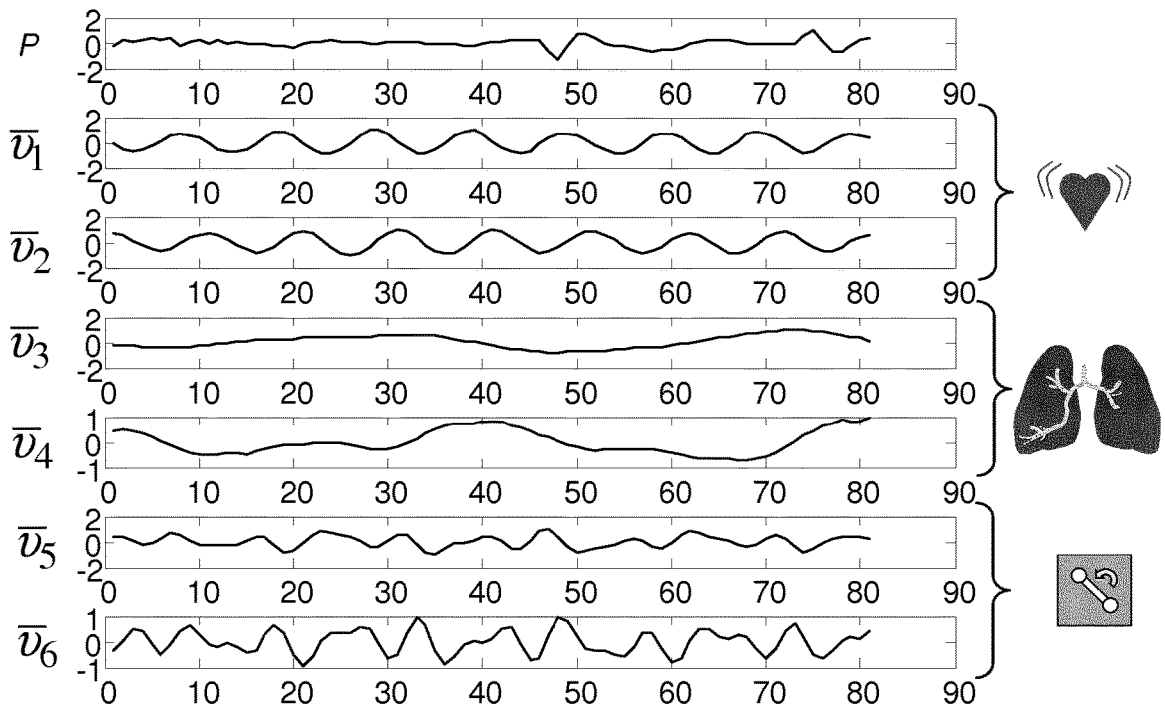
FIG. 11(c) illustrates an ordered set of eigenvectors computed for an arterial pressure signal, before VND.

There are other ways of using the arterial pressure signal. As a basis for the following discussion, FIG. 11(c) illustrates an arterial pressure signal P and the six most significant eigenvectors $\bar{v}_1, \ldots, \bar{v}_6$ computed by PCA when the fluid connection is intact, and these eigenvectors $\bar{v}_1, \ldots, \bar{v}_6$ and the associated eigenvalues are essentially unaffected by a disruption on the venous side of the fluid connection. FIG. 10(b) illustrates an embodiment of the device 7 which includes, in addition to the modules 40', 40 and 41 for processing the venous pressure signal, corresponding modules 140', 140, 141 for processing the arterial pressure signal. The source separation modules 41, 141 generate eigenvectors and associated eigenvalues for the respective pressure signal. In one implementation, the detection module 42 selects, based on the eigenvalues, one or more of the most significant eigenvectors for the venous pressure signal (denoted "venous eigenvectors") and one or more corresponding eigenvectors for the arterial pressure signal (denoted "arterial eigenvectors"). The detection module 42 then cross-correlates the venous and arterial eigenvector(s), determines the maximum correlation value for each cross-correlation, and computes the monitoring parameter based on the maximum correlation value(s). The monitoring parameter reflects the change among the venous eigenvectors represented by the transition from FIG. 11(a) to FIG. 11(b), since the correlation value between venous and arterial eigenvectors with the same order number is likely to change (decrease) when the fluid connection is disrupted. In another implementation, the detection module 42 computes the monitoring parameter as a single or accumulated difference between one or more eigenvalues for the venous pressure signal (denoted "venous eigenvalues") and one or more corresponding eigenvalues for the arterial pressure signal (denoted "arterial eigenvalues"). This difference may change when the fluid connection is disrupted.

It should be noted that the patient pulses need not dominate the pressure signal for the monitoring technique to work. When the pump pulses are stronger than the patient pulses, a number of the most significant eigenvectors and the associated eigenvalues will represent the pump pulses. It may thus be advantageous to adapt the computation of the monitoring parameter in step 506 to this situation, e.g. to select the eigenvalues/eigenvectors so as to exclude or minimize the impact of the pump pulses. Likewise, if the pressure signal has a non-zero mean, the computation of the monitoring parameter may be adapted to exclude one or more of the most significant eigenvectors and the associated eigenvalues.

Reverting to FIG. 5, it should be understood that the signal vectors in step 504 may be populated to correspond not only to time-shifted signal segments in one pressure signal but also to correspond to one or more other signal segments, which may or may not be time-shifted. These other signal segments are retrieved from one or more other pressure signals, e.g. the arterial pressure signal.

In yet another variant, at least a subset of the signal vectors in step 504 may be populated to correspond a plurality of time-shifted signal segments in an intermediate signal which is formed, e.g. in step 502, as a linear combination of pressure values in overlapping (time-synchronized) signal segments in two or more pressure signals. The intermediate signal is thus an artificial pressure signal that comprises a time-sequence of pressure values and is generated for the purpose of populating the signal vectors. It can be shown that computing eigenvectors/eigenvalues based on signal vectors given by time-shifted segments in such an intermediate signal is mathematically equivalent to computing eigenvectors/eigenvalues based on signal vectors given by time-shifted segments in the pressure signals that are linearly combined into the intermediate signal. The skilled person is readily able to modify all of the devices 7 disclosed herein to generate and use such an intermediate signal. Taking the device 7 in FIG. 6 as an example, the intermediate signal may be generated by the extraction module 40, or by the source separation module 41 before or while it populates the signal vectors.

Irrespective of representation, the monitoring device 7 may be implemented by special-purpose software (or firmware) run on one or more general-purpose or special-purpose computing devices. In this context, it is to be understood that an "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units (cf. 8 in FIG. 1), e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The device 7 may further include a system memory and a system bus that couples various system components including the system memory (cf. 9 in FIG. 1) to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The device 7 may include one or more communication interfaces, such as a serial interface, a parallel interface, a USB interface, a wireless interface, a network adapter, etc, as well as one or more data acquisition devices, such as an A/D converter. The special-purpose software may be provided to the device 7 on any suitable computer-readable medium, including a record medium or a read-only memory.

It is also conceivable that some (or all) elements/means are fully or partially implemented by dedicated hardware, such as an FPGA, an ASIC, or an assembly of discrete electronic components (resistors, capacitors, operational amplifier, transistors, filters, etc), as is well-known in the art.

It should be emphasized that the invention is not limited to digital signal processing, but could be fully implemented by a combination of analog devices.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The inventive monitoring technique may be applied to detect a disruption of a fluid connection between all types of fluid containing systems, by processing one or more pressure signals acquired from a set of pressure sensors in one ("the first") of the fluid containing systems and aiming at detecting, in the presence of pulsations ("first pulses") from a pulse generator in or associated with the first fluid containing system, a disappearance/decrease of pulsations ("second pulses") originating from a pulse generator in or associated with the other ("the second") fluid containing system. In this context, "associated with" implies that the pulse generator need not be included in the fluid containing system but is capable of generating pressure waves that propagate in the fluid containing system to the pressure sensor(s).

For example, the first fluid containing system may be any type of EC circuit in which blood is taken from the systemic blood circuit of the patient to have a process applied to it before it is returned to the patient. Such EC circuits include circuits for hemodialysis, hemofiltration, hemodiafiltration, plasmapheresis, apheresis, extracorporeal membrane oxygenation, assisted blood circulation, and extracorporeal liver support/dialysis. Other types of EC circuits that may form the first fluid containing system include circuits for blood transfusion, as well as heart-lung-machines.

The inventive technique is also applicable for detection of a disruption of a fluid connection between the cardiovascular system of a human or animal subject and fluid systems that contain other liquids than blood, including systems for intravenous therapy, infusion pumps, automated peritoneal dialysis (APD) systems, etc. Examples of such liquids include medical solutions, dialysis fluids, infusion liquids, water, etc.

It should be emphasized that the fluid connection need not be established with respect to a human or animal subject. For example, the fluid connection may be defined between a regeneration system for dialysis fluid and a supply of dialysis fluid, where the regeneration system circulates dialysis fluid from the supply through a regeneration device and back to the supply. In another example, the fluid connection is defined between a supply of priming fluid and an EC circuit. In a further example, the fluid connection is defined between a water purification system and a water supply.

The first pulse generator may be any type of pumping device, not only rotary peristaltic pumps as disclosed above but also other types of positive displacement pumps, such as linear peristaltic pumps, diaphragm pumps, as well as centrifugal pumps. Further, the pulse generator may be one or more valves or flow restrictors that are installed in or associated with the first fluid containing system. The valves and flow restrictors may be operable to intermittently stop a flow of fluid, change a flow rate of fluid, or change a fluid flow path. The valves and flow restrictors may also be included in a system for degassing of a fluid or a system for changing the static pressure of a fluid. In another example, the pulse generator is a balancing chamber as used in certain types of dialysis systems.

Similarly, the second pulse generator may be any type of pulse generator, be it human or mechanic.

The invention claimed is:

1. A monitoring device for detecting a disruption of a fluid connection between a first fluid containing system comprising a first pulse generator and a second fluid containing system comprising a second pulse generator, said monitoring device comprising:
   an input for receiving at least one pressure signal from a set of pressure sensors arranged in the first fluid containing system to detect first pulses originating from the first pulse generator and second pulses originating from the second pulse generator; and
   a signal processor connected to the input and being configured to:
      populate a plurality of signal vectors of identical length such that each of the signal vectors corresponds to a respective signal segment of signal values in the at least one pressure signal;
      process the signal vectors by a source separation algorithm so as to compute one or more eigenvector and/or one or more eigenvalue associated with the signal vectors; and
      detect the disruption based on a monitoring parameter, which is computed as a function of the one or more eigenvector and/or the one or more eigenvalue to be responsive to the second pulses in the at least one pressure signal.

2. The monitoring device of claim 1, wherein the signal processor is configured, when processing the signal vectors by the source separation algorithm, to compute the one or more eigenvector and/or the one or more eigenvalue for an estimated covariance matrix comprising estimated covariance values for the signal vectors.

3. The monitoring device of claim 2, wherein the estimated covariance matrix is given by $f(X^T X)$, wherein X is a matrix with the signal vectors arranged as rows or columns, $X^T$ is a transpose of the matrix X, and $f$ is a linear function.

4. The monitoring device of claim 2, wherein the signal processor is further configured, when processing the signal vectors, to:
compute the estimated covariance values,
populate the estimated covariance matrix by the estimated covariance values, and
process the estimated covariance matrix for computation of the one or more eigenvector and/or the one or more eigenvalue.

5. The monitoring device of claim 1, wherein the source separation algorithm comprises one of Principal Component Analysis, PCA, and Independent Component Analysis, ICA.

6. The monitoring device of claim 1, wherein the signal processor is configured to populate the signal vectors such that at least a subset of the signal vectors corresponds to mutually time-shifted signal segments in a dedicated pressure signal included among the at least one pressure signal, or in an intermediate signal generated based on the at least one pressure signal.

7. The monitoring device of claim 6, wherein the signal processor is configured to populate the signal vectors such that said at least a subset of the signal vectors corresponds to partly overlapping and mutually time-shifted signal segments in the dedicated pressure signal or the intermediate signal.

8. The monitoring device of claim 6, wherein the signal processor is configured to populate the signal vectors exclusively based on the mutually timeshifted signal segments in the dedicated pressure signal or the intermediate signal.

9. The monitoring device of claim 1, wherein the at least one pressure signal comprises a plurality of pressure signals from a plurality of pressure sensors, and wherein the signal processor is configured to populate the signal vectors such that each signal vector corresponds to a respective signal segment from a respective one of the plurality of pressure signals.

10. The monitoring device of claim 1, wherein the signal processor is further configured, when detecting the disruption, to identify a change to the monitoring parameter over time or compare the monitoring parameter to a threshold value.

11. The monitoring device of claim 1, wherein the signal processor is configured, when processing the signal vectors, to compute a plurality of eigenvalues, and
wherein the signal processor is further configured to compute the monitoring parameter to represent one of:
a magnitude of at least a subset of the plurality of eigenvalues,
a difference between pairs of eigenvalues for at least a subset of the plurality of eigenvalues when ordered by magnitude, and
a distribution of at least a subset of the plurality of eigenvalues when ordered by magnitude.

12. The monitoring device of claim 1, wherein the signal processor is configured, when processing the signal vectors, to compute a plurality of eigenvalues and/or a plurality of eigenvectors, and wherein the signal processor is further configured, when computing the monitoring parameter, to order the eigenvectors and/or the eigenvalues by order of magnitude of the eigenvalues.

13. The monitoring device of claim 12, wherein the signal processor is configured to compute the monitoring parameter based on at least one selected eigenvector among the plurality of eigenvectors and/or at least one selected eigenvalue among the plurality of eigenvalues, and wherein the signal processor is configured to derive each selected eigenvalue by selecting an eigenvalue having a predefined order number among the plurality of eigenvalues when ordered by magnitude, and/or to derive each selected eigenvector by selecting an eigenvector having a predefined order number among the plurality of eigenvectors when ordered by magnitude of their associated eigenvalues.

14. The monitoring device of claim 13, wherein the signal processor is configured to compute the monitoring parameter to represent a magnitude of the at least one selected eigenvalue.

15. The monitoring device of claim 13, wherein the signal processor is configured to compute the monitoring parameter to represent one of:
a frequency of the at least one selected eigenvector, and
a shape of the at least one selected eigenvector.

16. The monitoring device of claim 1, wherein the signal processor is configured to receive, via the input, a reference pressure signal from a reference pressure sensor in the set of pressure sensors in the first fluid containing system, the reference pressure sensor being arranged to detect the second pulses irrespective of the disruption of the fluid connection,
wherein the signal processor is further configured to:
populate a plurality of reference signal vectors of identical length such that each of the reference signal vectors corresponds to a respective signal segment of signal values in the reference pressure signal, and
process the reference signal vectors by the source separation algorithm so as to compute at least one of: one or more reference eigenvector and one or more reference eigenvalue associated with the reference signal vectors,
wherein the signal processor is configured, when detecting the disruption, to compare the one or more eigenvector to the one or more reference eigenvector and/or compare the one or more eigenvalue to the one or more reference eigenvalue.

17. The monitoring device of claim 16, wherein the signal processor is configured to compute the monitoring parameter as a function of a correlation value resulting from a cross-correlation of at least one selected eigenvector and the one or more reference eigenvector.

18. The monitoring device of claim 1, wherein the signal processor is further configured, before populating the plurality of signal vectors to filter the at least one pressure signal so as to decrease a magnitude of the first pulses below a magnitude of the second pulses.

19. The monitoring device of claim 1, wherein the signal processor is further configured, before processing the signal vectors, to process the at least one pressure signal and/or the signal vectors to yield an average of zero for signal vector values in a respective signal vector.

20. The monitoring device of claim 1, wherein the first fluid containing system is an extracorporeal blood circuit comprising a blood pump configured to pump blood from a blood withdrawal device to a blood return device, wherein the second fluid containing system is a cardiovascular system of a human body, the first pulse generator comprising the blood pump and the second pulses originating from a pulse generator in or attached to the human body, wherein the blood withdrawal device and the blood return device are fluidly connected to the cardiovascular system, and wherein the fluid connection is formed between the blood return device and the cardiovascular system.

21. The monitoring device of claim 20, wherein the signal processor is configured to receive, via the input, the at least one pressure signal from a pressure sensor located between the blood pump and the blood return device to sense the pressure of the blood in the extracorporeal blood circuit.

22. The monitoring device of claim 1, wherein the signal processor is further configured to generate an output signal indicative of the disruption of the fluid connection.

23. A monitoring device for detecting a disruption of a fluid connection between a first fluid containing system comprising a first pulse generator and a second fluid containing system comprising a second pulse generator, said monitoring device comprising:
    means for receiving at least one pressure signal from a set of pressure sensors arranged in the first fluid containing system to detect first pulses originating from the first pulse generator and second pulses originating from the second pulse generator;
    means for populating a plurality of signal vectors of identical length such that each of the signal vectors corresponds to a respective signal segment of signal values in the at least one pressure signal;
    means for processing the signal vectors by a source separation algorithm so as to compute one or more eigenvector and/or one or more eigenvalue associated with the signal vectors; and
    means for detecting the disruption based on a monitoring parameter, which is computed as a function of the one or more eigenvector and/or the one or more eigenvalue to be responsive to the second pulses in the at least one pressure signal.

24. A method of monitoring a fluid connection between a first fluid containing system comprising a first pulse generator and a second fluid containing system comprising a second pulse generator, said method being performed by a data processor and comprising:
    receiving at least one pressure signal from a set of pressure sensors arranged in the first fluid containing system to detect first pulses originating from the first pulse generator and second pulses originating from the second pulse generator;
    populating a plurality of signal vectors of identical length such that each of the signal vectors corresponds to a respective signal segment of signal values in the at least one pressure signal;
    processing the signal vectors by a source separation algorithm so as to compute one or more eigenvector and/or one or more eigenvalue associated with the signal vectors; and
    detecting the disruption based on a monitoring parameter, which is computed as a function of the one or more eigenvector and/or the one or more eigenvalue to be responsive to the second pulses in the at least one pressure signal.

25. A computer-readable medium comprising processing instructions for causing the data processor to perform the method of claim 24.

* * * * *